(12) United States Patent
Butterfield et al.

(10) Patent No.: US 11,636,937 B2
(45) Date of Patent: *Apr. 25, 2023

(54) MODEL-BASED INFUSION SITE MONITOR

(71) Applicant: CareFusion 303, Inc., San Diego, CA (US)

(72) Inventors: Robert Dwaine Butterfield, Poway, CA (US); Brian Stock, Renton, WA (US); Melissa Strait, Aurora, CA (US); Harry Dudley, Pasadena, CA (US); Stephen Rosenthal, Bethlehem, PA (US)

(73) Assignee: CAREFUSION 303, INC., San Diego, CA (US)

( * ) Notice: Subject to any disclaimer, the term of this patent is extended or adjusted under 35 U.S.C. 154(b) by 822 days.

This patent is subject to a terminal disclaimer.

(21) Appl. No.: 16/450,777

(22) Filed: Jun. 24, 2019

(65) Prior Publication Data

US 2019/0365983 A1 Dec. 5, 2019

Related U.S. Application Data

(63) Continuation of application No. 15/369,650, filed on Dec. 5, 2016, now Pat. No. 10,328,199, which is a
(Continued)

(51) Int. Cl.
*A61M 5/14* (2006.01)
*G16H 20/17* (2018.01)
(Continued)

(52) U.S. Cl.
CPC .............. *G16H 20/17* (2018.01); *A61M 5/14* (2013.01); *A61M 5/142* (2013.01);
(Continued)

(58) Field of Classification Search
CPC .......... A61M 5/16836; A61M 5/16859; A61M 5/16854; A61M 5/16831; A61M 2205/18; A61M 2205/52; G06F 19/3468
See application file for complete search history.

(56) References Cited

U.S. PATENT DOCUMENTS 4,898,576 A * 2/1990 Philip ............... A61M 5/16859
604/65
5,609,576 A 3/1997 Voss et al.
(Continued)

FOREIGN PATENT DOCUMENTS

EP 387724 9/1990
JP 6365876 3/1988
(Continued)

OTHER PUBLICATIONS

Canadian Office Action for Application No. 2760836, dated Aug. 8, 2016, 5 pages.
(Continued)

*Primary Examiner* — Nathan R Price
*Assistant Examiner* — Anh Bui
(74) *Attorney, Agent, or Firm* — Morgan, Lewis & Bockius LLP

(57) ABSTRACT

A medication delivery monitoring device is disclosed. The device includes a user interface configured to receive input information, and a sensor configured to measure a plurality of fluid state parameters of a fluid delivery channel through which the medication is delivered by a vascular access device (VAD) to an infusion site region of the patient. The device also includes a processor configured to determine a state of the infusion site region based on the plurality of measured fluid state parameters and the input information, and an output device configured to provide a communication regarding the state of the infusion site region. Methods and
(Continued)

computer-readable mediums for monitoring medication delivery are also disclosed.

21 Claims, 17 Drawing Sheets

Related U.S. Application Data continuation of application No. 13/319,081, filed as application No. PCT/US2010/033793 on May 5, 2010, now Pat. No. 9,514,279.

(60) Provisional application No. 61/175,545, filed on May 5, 2009.

(51) Int. Cl.
*A61M 5/168* (2006.01)
*G16H 50/50* (2018.01)
*G16Z 99/00* (2019.01)
*A61M 5/142* (2006.01)

(52) U.S. Cl.
CPC .... *A61M 5/16831* (2013.01); *A61M 5/16836* (2013.01); *A61M 5/16854* (2013.01); *A61M 5/16859* (2013.01); *G16H 50/50* (2018.01); *G16Z 99/00* (2019.02); *A61M 2205/18* (2013.01); *A61M 2205/3334* (2013.01); *A61M 2205/3576* (2013.01); *A61M 2205/502* (2013.01); *A61M 2205/52* (2013.01); *Y02A 90/10* (2018.01)

(56) References Cited

U.S. PATENT DOCUMENTS

| | | | |
|---|---|---|---|
| 5,713,856 A | 2/1998 | Eggers et al. | |
| 6,375,624 B1* | 4/2002 | Uber, III | A61M 5/16836 600/549 |
| 6,562,001 B2 | 5/2003 | Lebel et al. | |
| 6,689,089 B1 | 2/2004 | Tiedtke et al. | |
| 6,936,029 B2 | 8/2005 | Mann et al. | |
| 7,025,743 B2 | 4/2006 | Mann et al. | |
| 7,083,593 B2 | 8/2006 | Stultz | |
| 7,147,615 B2 | 12/2006 | Wariar et al. | |
| 7,320,676 B2 | 1/2008 | Miesel | |
| 7,678,071 B2 | 3/2010 | Lebel et al. | |
| 9,514,279 B2 | 12/2016 | Butterfield et al. | |
| 10,328,199 B2* | 6/2019 | Butterfield | A61M 5/16854 |
| 2001/0037093 A1 | 11/2001 | Benkowski et al. | |
| 2003/0065308 A1 | 4/2003 | Lebel et al. | |
| 2003/0171738 A1 | 9/2003 | Konieczynski et al. | |
| 2003/0191431 A1 | 10/2003 | Mann et al. | |
| 2004/0193453 A1 | 9/2004 | Butterfield et al. | |
| 2005/0113745 A1 | 5/2005 | Stultz | |
| 2005/0137530 A1 | 6/2005 | Campbell et al. | |
| 2005/0171513 A1 | 8/2005 | Mann et al. | |
| 2005/0177096 A1 | 8/2005 | Bollish et al. | |
| 2005/0256447 A1 | 11/2005 | Richardson et al. | |
| 2006/0135940 A1 | 6/2006 | Joshi | |
| 2006/0173444 A1 | 8/2006 | Choy et al. | |
| 2008/0125759 A1 | 5/2008 | Konieczynski et al. | |
| 2008/0147050 A1 | 6/2008 | Mann et al. | |
| 2008/0188796 A1 | 8/2008 | Steil et al. | |
| 2009/0124964 A1 | 5/2009 | Leach et al. | |
| 2009/0192366 A1 | 7/2009 | Mensinger et al. | |
| 2010/0137842 A1 | 6/2010 | Gibson | |
| 2010/0280446 A1 | 11/2010 | Kalpin | |

FOREIGN PATENT DOCUMENTS

| | | |
|---|---|---|
| JP | H07124125 | 5/1995 |
| JP | 10503688 | 7/1998 |
| JP | 2005516637 | 6/2005 |
| WO | WO-2007033103 A1 | 3/2007 |
| WO | WO-2008008281 | 1/2008 |
| WO | WO-2009042577 | 4/2009 |

OTHER PUBLICATIONS

English Language Translation of Japanese Notification of Reasons for Refusal in Japanese Patent Application No. 2012-509958 dated Oct. 28, 2014, 2 pages.
European Office Action for Application No. 10717436.9, dated Aug. 14, 2017, 5 pages.
Indian Office Action for Application No. 8181/CHENP/2011, dated May 28, 2019, 6 pages.
International Preliminary Report on Patentability for Application No. PCT/US2010/033793, 21 pages.
Korean Office Action for Application No. Oct. 2011-7027177, dated Feb. 24, 2016, 7 pages excluding English summary.

* cited by examiner

| Term | Equation |
|---|---|
| Body interstitium fluid volume | $dV_B/dt = J_{C_B} - J_{L_B} - (1-prop)J_{per}$ |
| Body interstitium protein mass | $dM_B/dt = Q_{C_B} - Q_{L_B}$ |
| Arm interstitium fluid volume | $dV_A/dt = J_{C_A} - J_{L_A} - (prop)J_{per}$ |
| Arm interstitium protein mass | $dM_A/dt = Q_{C_A} - Q_{L_A}$ |
| Plasma fluid volume | $dV_{PL}/dt = (J_{L_B} + J_{L_A}) - (J_{C_B} + J_{C_A}) + J_{in} + J_{iv} - J_{ur}$ |
| Plasma protein mass | $dM_{PL}/dt = (Q_{L_B} + Q_{L_A}) - (Q_{C_B} + Q_{C_A})$ |
| Plasma protein concentration | $C_{PL} = M_{PL}/V_{PL}$ |
| Body interstitium available protein concentration | $C_B = M_B/(V_B - (1-prop) \cdot V_{I,EX})$ |
| Arm interstitium available protein concentration | $C_A = M_A/(V_A - prop \cdot V_{I,EX})$ |
| Body interstitium colloid osmotic pressure | $\Pi_B = C_B/1.522$ |
| Arm interstitium colloid osmotic pressure | $\Pi_A = C_A/1.522$ |
| Plasma colloid osmotic pressure | $\Pi_{PL} = C_{PL}/1.522$ |
| Body interstitium fluid hydrostatic pressure | $P_B = f(V_B)$, see Appendix C |
| Arm interstitium fluid hydrostatic pressure | $P_A = f(V_A)$, see Appendix C |
| Capillary fluid hydrostatic pressure | $P_C = P_{C_0} + 0.0096(V_{PL} - V_{PL_0})$ |
| Body transcapillary fluid flow | $J_{C_B} = (1-prop)\kappa[(P_{PL} - P_B) - \sigma(\Pi_{PL} - \Pi_B)]$ |
| Arm transcapillary fluid flow | $J_{C_A} = prop \cdot \kappa[(P_{PL} - P_A) - \sigma(\Pi_{PL} - \Pi_A)]$ |
| Lymph fluid flow from body | $J_{L_B} = (1-prop)(J_{L_0} + \lambda(P_B - P_{B_0}))$ |
| Lymph fluid flow from arm | $J_{L_A} = prop(J_{L_0} + \lambda(P_A - P_{A_0}))$ |
| Body transcapillary protein exchange rate | $Q_{C_B} = (1-\sigma)J_{C_B}\left[\dfrac{C_{PL} - C_{B,AV} \cdot e^{-(1-\sigma)J_{C_B}/(\mu(1-prop))}}{1 - e^{-(1-\sigma)J_{C_B}/(\mu(1-prop))}}\right]$ |
| Arm transcapillary protein exchange rate | $Q_{C_A} = (1-\sigma)J_{C_A}\left[\dfrac{C_{PL} - C_{A,AV} \cdot e^{-(1-\sigma)J_{C_B}/(\mu \cdot prop)}}{1 - e^{-(1-\sigma)J_{C_A}/(\mu \cdot prop)}}\right]$ |
| Lymph protein removal rate from body | $Q_{L_B} = J_{L_B} \cdot C_B$ |
| Lymph protein removal rate from arm | $Q_{L_A} = J_{L_A} \cdot C_A$ |

FIG. 3H

| Parameter | Description | Value | Units |
|---|---|---|---|
| $V_{PL_0}$ | Normal plasma volume | 3200 | ml |
| $V_{I_0}$ | Normal interstitium volume | 8400 | ml |
| $V_{I,EX}$ | Excluded interstitium volume | 2100 | ml |
| $\Pi_{PL_0}$ | Normal plasma colloid osmotic pressure | 25.9 | mmHg |
| $\Pi_{I_0}$ | Normal interstitium colloid osmotic pressure | 14.7 | mmHg |
| $C_{PL_0}$ | Normal plasma protein concentration | 39.4 | g/l |
| $C_{I_0}$ | Normal interstitium protein concentration | 16.8 | g/l |
| $C_{I,AV_0}$ | Normal interstitium available protein concentration | 22.4 | g/l |
| $Q_{PL_0}$ | Normal plasma protein mass | 126.1 | g |
| $Q_{I_0}$ | Normal interstitium protein mass | 141.1 | g |
| $P_{I_0}$ | Normal (body) interstitium fluid hydrostatic pressure | -0.7 | mmHg |

FIG. 3I

MODEL-BASED INFUSION SITE MONITOR

This application is a continuation of U.S. application Ser. No. 15/369,650 filed Dec. 5, 2016, now U.S. Pat. No. 10,328,199, and U.S. application Ser. No. 13/319,081 filed Jan. 23, 2012, now U.S. Pat. No. 9,514,279, which is the U.S. National Phase under 35 U.S.C. § 371 of International Application No. PCT/US2010/033793, filed on May 5, 2010 and published in English on Nov. 11, 2010, which claims the benefit from U.S. Provisional No. 61/175,545, filed May 5, 2009, the entirety of each of which is incorporated herein by reference.

TECHNICAL FIELD

The present disclosure generally relates to management of infusion medications, and more particularly, to a system for detecting abnormalities in the flow of infusion medications to a patient.

DESCRIPTION OF THE RELATED ART

Many individuals suffer from chronic health problems, the treatment of which requires regular, and sometimes extended, intravenous medication deliveries. Certain treatment regimens for diseases such as diabetes, asthma, epilepsy, cancer and even allergies, require the regular and sequenced infusion of precise amounts of intravenous medication for the patient's survival. Intravenous infusion of medications can take on many forms depending on the patient, treatment regimen, and choices of the clinician and institution. Many infusions are provided via "central" lines which empty into the great vessels near the heart, such as the common vena cava, or directly into the heart, such as via the right atrium. Infusions are generally provided through vascular access devices (VAD), such as catheters, needles or IV cannulas. These may be placed in vessels, such as in the head (e.g., scalp needles), foot (e.g., in the dorsalis pedis vein), the dorsal side of the hand, the wrist, and the inner aspect of the elbow, known as the antecubital region. An 'infiltration' or 'extravasation' occurs when medication is accidentally infused into the tissue surrounding the VAD puncture site or the VAD outlet. There may be both significant injury to the tissue as well as loss of medication delivery to the target organ. The hyperosmotic, hypertonic nature of even ordinary IV fluids used in infusions, such as saline and dextrose, may cause localized damage leading to nerve injury, tissue necrosis, and infection. For centrally located catheters, penetration of the VAD outlet into the thorax, particularly into the pericardial sac surrounding the heart may be life threatening.

DISCLOSURE OF THE INVENTION

What is needed is a system and/or method to determine whether medication is being infused into a tissue region surrounding a VAD puncture site or VAD outlet. Accordingly, the systems and methods described herein advantageously feature determining an estimated state of an infusion site region (ISR), and outputting an alert, alarm and/or graphical/numerical indication of the state when the estimated state of the infusion site region and a plurality of actual fluid state parameters of a fluid delivery channel to the infusion site region indicate an infiltration. The estimated state of the infusion site region is, in certain embodiments, determined using either a compartment model of the infusion site region or a continuum model of the infusion site region.

According to certain embodiments of the present disclosure, a medication delivery monitoring device is provided. The device includes a user interface configured to receive input information, and a sensor configured to measure a plurality of fluid state parameters of a fluid delivery channel through which the medication is delivered by a vascular access device (VAD) to an infusion site region of the patient. The device also includes a processor configured to determine a state of the infusion site region based on the plurality of measured fluid state parameters and the input information, and an output device configured to provide a communication regarding the state of the infusion site region.

According to certain embodiments of the present disclosure, a method for monitoring medication delivery is provided. The method includes receiving input information and measuring a plurality of fluid state parameters of a fluid delivery channel through which the medication is delivered by a vascular access device (VAD) to an infusion site region of the patient. The method also includes determining a model state of the infusion site region based on the plurality of measured fluid state parameters and the input information, and providing a communication regarding the state of the infusion site region.

According to certain embodiments of the present disclosure, a computer-readable medium including computer-readable instructions for causing a processor to execute a method for monitoring medication delivery is provided. The method includes receiving input information and measuring a plurality of fluid state parameters of a fluid delivery channel through which the medication is delivered by a vascular access device (VAD) to an infusion site region of the patient. The method also includes determining a model state of the infusion site region based on the plurality of measured fluid state parameters and the input information, and providing a communication regarding the state of the infusion site region.

The accompanying drawings, which are included to provide further understanding and are incorporated in and constitute a part of this specification, illustrate disclosed embodiments and together with the description serve to explain the principles of the disclosed embodiments. In the drawings:

FIG. 3H is a set of model equations for modeling an IV infiltration.

FIG. 3I is a collection of estimates of parameters for a normal adult for use with the disclosed compartment model.

DETAILED DESCRIPTION

There is a problem, in the delivery of fluid medication to an infusion site region of a patient, of injury resulting from the medication being infused into the interstitial tissue space (ITS). Previous attempts at monitoring the safety of such infusions have been inaccurate or ineffective in part owing to their failure to employ information concerning the patient, VAD, fluid and history. This and other problems are addressed and solved, at least in part, by embodiments of the present disclosure, which include a medication delivery monitoring device. The device includes a user interface configured to receive input information, and a sensor configured to measure a plurality of fluid state parameters of a fluid delivery channel through which the medication is delivered by a vascular access device (VAD) to an infusion site region of the patient. The device also includes a processor configured to determine a state of the infusion site region based on the plurality of measured fluid state parameters and the input information, and an output device configured to provide a communication regarding the state of the infusion site region.

In the following detailed description, numerous specific details are set forth to provide a full understanding of the present disclosure. It will be obvious, however, to one ordinarily skilled in the art that the embodiments of the present disclosure may be practiced without some of these specific details. In other instances, well-known structures and techniques have not been shown in detail not to obscure the disclosure.

Figure 1:
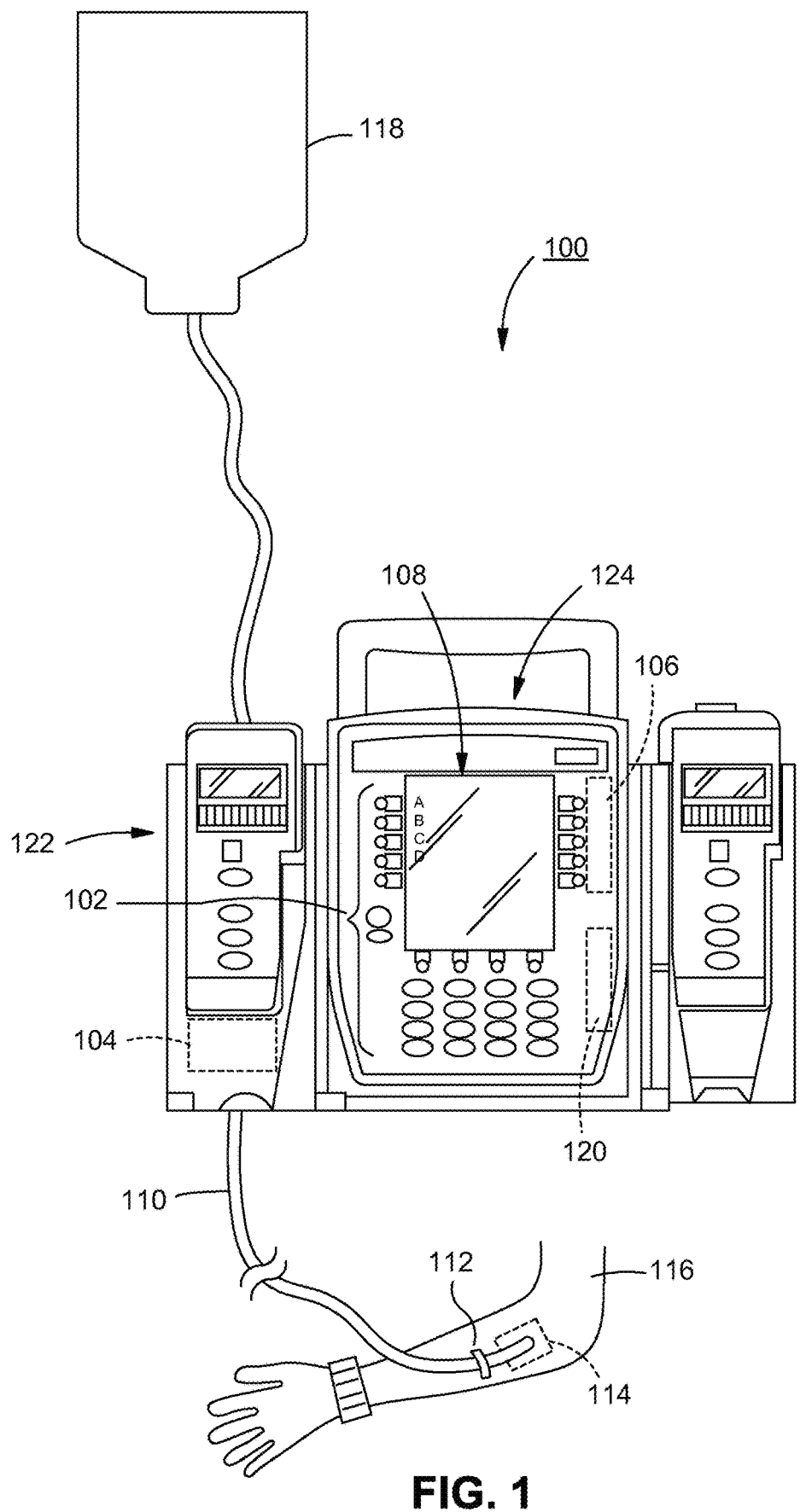
FIG. 1 illustrates a medication delivery monitoring system according to certain embodiments.

FIG. 1 illustrates a medication delivery monitoring system 100 according to certain embodiments. The system 100 includes a user interface 102, an outlet pressure sensor 104, and a processor 106. The system 100 is used, for example, with an infusion pump 122 (e.g., CareFusion's Alaris® System modular infusion pump line) or patient care unit 124 to monitor the infusion of a medication 118 from an intravenous (IV) bag through a fluid delivery channel 110 and into an infusion site region 114 of a patient 116 via a VAD. Both the infusion pump module 122, and patient care unit 124 (or "patient control unit" or "PCU" or "controller"), coupled to module 126, can comprise their own user interface, outputs (e.g., displays), and processor (e.g., for receiving pressure signals and controlling pumping). In certain embodiments, the system 100 (e.g., to measure resistance to modulate flow, As discussed herein, the terms "infusion site region." "ISR," "interstitial tissue space," "ITS," "IV site," and "IV site tissue" may be used interchangeably. Exemplary VADs include catheters, implanted ports, needles, and intravenous cannulas. In certain embodiments, the processor 106 is used to perform selected information processing, while a microcontroller embedded in the infusion pump module 122 is used for lower lever (e.g., fast, real-time) processing such as modulating the flow rate and process the received pressure signals to compute the flow resistance.

The user interface 102 is configured to receive input information (or "provided information") for the system 100, such as patient information, medication information, and/or VAD information, and output information through an output device 108. The patient information includes the weight of the patient, the height of the patient, the body surface area of the patient, the age of the patient, and/or the gender of the patient. In certain embodiments, the patient information includes the patient's diagnosis and treatment, which may impact factors such as a likelihood tissue at the infusion site region will be edematous. The medication information includes a chemical nature of the medication, a concentration of the medication, a rate of infusion dosage (e.g., ug/kg/min) and flow rate (e.g., mL/h) of the medication, and the nature of at least one diluent or additive associated with the medication. The VAD information includes a type of the VAD, a dimension of the VAD, the site in the body of the VAD, a compliance value of the VAD, a resistance value of the VAD, and a topology of the infusion network (e.g., which channels are infusing through the same VAD). In certain embodiments, the values include measurements, which is a static value that were either input via the user interface 102, stored in the PCU 124, and/or stored on a network connected to the PCU 124, such as on a server wirelessly in communication with the PCU 124. In certain embodiments, the VAD information may be available and received from a website (e.g., a website for the manufacturer of the VAD) with which the server is in communication. A wired or wireless input device can be used for the user interface 102, such as, but not limited to, a keyboard, a touch-screen display, a mouse, a microphone, a magnetic card reader, a biometric reader-sensor, a proximity reader, a radio frequency (RF) identification reader, and a symbology reader. In certain embodiments, acquisition of the parameters mentioned above are, at least in part, performed through an electronic communication of information, such as by using an optical barcode or radio frequency identification (RFID) linkage between a patient care unit or infusion pump and the system 100, to relieve a clinician of the need to enter the information. In certain embodiments, a server connected to the system 100 (e.g., wirelessly or by wire) can acquire this information from extant sources, such as an admission, discharge, and transfer (ADT) system, a clinical laboratory, physician order entry (POE), and/or pharmacy.

The outlet pressure sensor 104 is configured to measure a plurality of fluid state parameters of the fluid delivery channel 110. The fluid state parameters include, for example, the instantaneous and rate of change of pressure of the fluid delivery channel, resistance of the fluid delivery channel, capacitance of the fluid delivery channel, and fluidic impedance of the fluid delivery channel. In certain embodiments, the pressure is measured at an outlet of the fluid delivery channel 110, such as at the infusion site region 114 where the medication 118 leaves the fluid delivery channel 110.

In certain embodiments, the fluidic input resistance to the infusion tubing network 110 is measured based on small scale modulations, introduced by the processor 106, in the average infusion rate of the medication 118. In certain embodiments, two basic approaches are employed to measure the fluidic intake resistance. One approach is used for rates above 50 mL/h. The remaining, more complex approach is used for rates at or below 50 mL/h. The higher rate approach, in principle, dynamically adjusts the flow rate typically in a square wave pattern around the mean programmed value and measures the pressure response to these modulations. The final pressure at the high rate is subtracted from the final pressure at the low rate and this difference divided by the difference in the flow rates. The result is a 'dynamic' input resistance of the fluid path. The resulting resistance is filtered using median and averaging methods to eliminate noise due to ambulation, etc. The lower flow method achieves a similar result, however, the modulation and the subsequent processing of the pressure signals is somewhat more complex in order to avoid undue variation in the flow pattern that could be undesirable for some medications. Additional information regarding approaches to measure fluidic input resistance can be found in U.S. Pat. Nos. 5,803,917 and 6,416,291, which are incorporated by reference herein in their entirety. The small scale modulations are associated with resulting pressure variations in the fluid delivery channel 110 to further measure the capacitance and the impedance at an input to the fluid delivery channel 110. In certain embodiments including those where fluid impedance is measured, the outlet pressure sensor 104 is configured to be of high resolution and of high accuracy.

The processor 106 is configured to determine a state of the infusion site region 114 based on the plurality of measured fluid state parameters and the input information. In certain embodiments, the processor 106 is configured to record at least one of instantaneous fluid state parameters, filtered fluid state parameters, and long term trends of fluid state parameters. The processor 106 is further configured to model the state of fluids and proteins (e.g., protein mass, tissue porosity) at the infusion site region 114 based on the pressure of the fluid delivery channel, resistance of the fluid delivery channel, and the input information (e.g., the patient information, medication information, and/or VAD information). In certain embodiments, the model is further based on the impedance of the fluid delivery channel. As discussed herein, in certain embodiments, the term 'impedance' incorporates the three orthogonal parameters of resistance, compliance and inertance. In certain embodiments, the model employs pump flow of the fluid delivery channel 118. In certain embodiments, the model is further employs the history of the measured fluid state parameters, such as the history of the infused medication 118 (e.g., volume of the infused medication over time). The history of the measured fluid state parameters (e.g., volume of the infused medication over time) is configured to be stored in a memory 120.

In certain embodiments, the model is either a discrete compartment model, a continuum model, or combination of both. The compartment model describes quantity and pressures of fluids and proteins (i.e., the major solute of blood plasma fluid) and from these derives the expected volumes, deformations and pressures in the tissue surrounding the infusion site region 114. The continuum model describes similar parameters but computes them employing a much higher resolution physical model of the elasticity and porosity of the ITS. The compartment model conceptualizes and segregates the body and its fluids into a small number of homogeneous regions, while the continuum or finite-element model describes the properties of the body and its fluids in three physical dimensions over time. In certain embodiments, the continuum model is employed in the course of refining the structure and parameters of the compartment model, and, with the appropriate processing power, is implemented directly in a real-time system.

The approaches complement each other since the compartment model simulates flow between distinct regions and the continuum model simulates flow within a region. Further detail regarding these models, as well as how they are generated, is described in further detail below. Based on a comparison of the model estimate of uninfiltrated and infiltrated states, the output device 108 is configured to provide a communication regarding the state of the infusion site region 114, such as to indicate that the infusion site region 114 has been infiltrated. For example, the model is configured to predict that no IV fluid is present in the ITS, which is the 'normal' state, and configured to predict any positive value of IVD as a progressively deteriorating condition.

Based on knowledge of IV flow, measured pressure and resistance and parameters such as compliance and porosity which correlate with operator-entered patient parameters such as age and IV VAD location, the model predicts the state of the interstitial tissue including amounts of fluid added to the interstitial space, amount of protein transported and expected pressure values. If the fluid state parameters measured by the sensor 104 are not within a pre-determined range of the corresponding expected fluid state parameters, then the processor 106 sends a communication to the output device 108. In certain embodiments, the output communication is an alert, alarm and/or graphical/numerical indication of the state. The output communication is, in certain embodiments, a threshold driven event. In certain embodiments, the output communication presents the state of the interstitial tissue as a continuous variable with and without generation of an alarm/alert event. In certain embodiments, a communication can be sent based on other properties associated with the patient, such as, but not limited to, (1) the fluid volume, pressure, compliance, and resistance infusion pathway, (2) the fluid volume, pressure, protein mass, compliance, and porosity of an interstitial tissue matrix, (3) and the fluid volume, pressure, protein mass, compliance, and resistance of a peripheral vessel. The rates of change of these values may, in certain embodiments, be an independent parameter of state. For example, determining the compliance of an infiltrated tissue site region surrounding the vessel site might, in certain embodiments, be determined by trending the rate of change of pressure against volume pumped. As compared to a vessel, where compliance is generally high, and pressure generally does not change over a given volume of fluid infused, in the infiltrated tissue site, pressure can increase over time, depending on pump flow rate and its relation to lymphatic uptake, during at least part of the course of the infiltration. For example, at 20 mL/h, it is expected that lymphatic uptake would be overwhelmed in a 10 kg child, thus if the vessel wall is breached by the cannula, pressure would be expected to increase for a period of time. The disclosed compartment model predicts that as pressure rises, fluid begins to diffuse away more quickly so that ultimately a relatively steady state pressure is attained.

Once the output device 108, which is illustrated in FIG. 1 as a display, receives the communication, the output device 108 is configured to display the communication, such as in the form of a value, an alert, or an alarm. The communication can be, for example, a visible communication (e.g., an onscreen message or a graphical indicator such as a bar graph or trend plot), an audible communication (e.g., a beeping alarm), a different type of sensory communication (e.g., a vibration), or any combination thereof. In certain embodiments, the output device 108 is configured to display both current and expected fluid state parameters throughout the time the medication 118 is infused into the patient 116, regardless of whether the expected fluid state parameters indicate an infiltration. Such display is advantageous in that it provides an operator with a continuing status of the infusion site region 114 of the patient 116. In certain embodiments, the output device 108 is configured to display a deviation of the current fluid state parameters from expected fluid state parameters. For example, if the expected IV fluid in an ITS is zero, the output device 108 will display the model estimate of the IV fluid that is present in the ITS. In certain embodiments, the communication includes an estimate, by the disclosed model, of a key state variable, e.g., the estimated intravenous fluid in the infusion site region 114, which should, under normal conditions, be zero. In certain embodiments, as disclosed above, the estimated key state variable is presented, by the output device, such as to allow a clinician to allow the clinician to decide if any action is appropriate. In certain embodiments, the estimated key state variable is used as an alarm threshold by the output device. In certain embodiments, the threshold can depend on the size of the patient's infusion site region 114 (e.g. an infusion site region 114 for an adult, child, or neonate), the likely toxicity of the medication, e.g., for a highly vesicant infusion, the threshold should be lower than a saline solution infusion for hydration.

The output device 108 is illustrated as a display. Other types of output devices 108 can be used, including, without limitation, a printer, audible indicators such as speakers, or other visual indicators such as display screens, including a cathode ray tube (CRT) display, vacuum fluorescent display (VFD), light emitting diode (LED) display, plasma display panel (PDP), liquid crystal display (LCD), organic light emitting diode (OLED), or surface-conduction electron-emitter display (SED). Similarly, the communication provided to the output device 108 can be, for example, a visible communication (e.g., an onscreen message), an audible communication (e.g., a beeping alarm), a different type of sensory communication (e.g., a vibration), or any combination thereof. The output device 108 is configured to display or otherwise output information provided by the processor 106, such as communications identifying whether the measured fluid state parameters are within a pre-defined range of the expected fluid state parameters.

Figure 2:
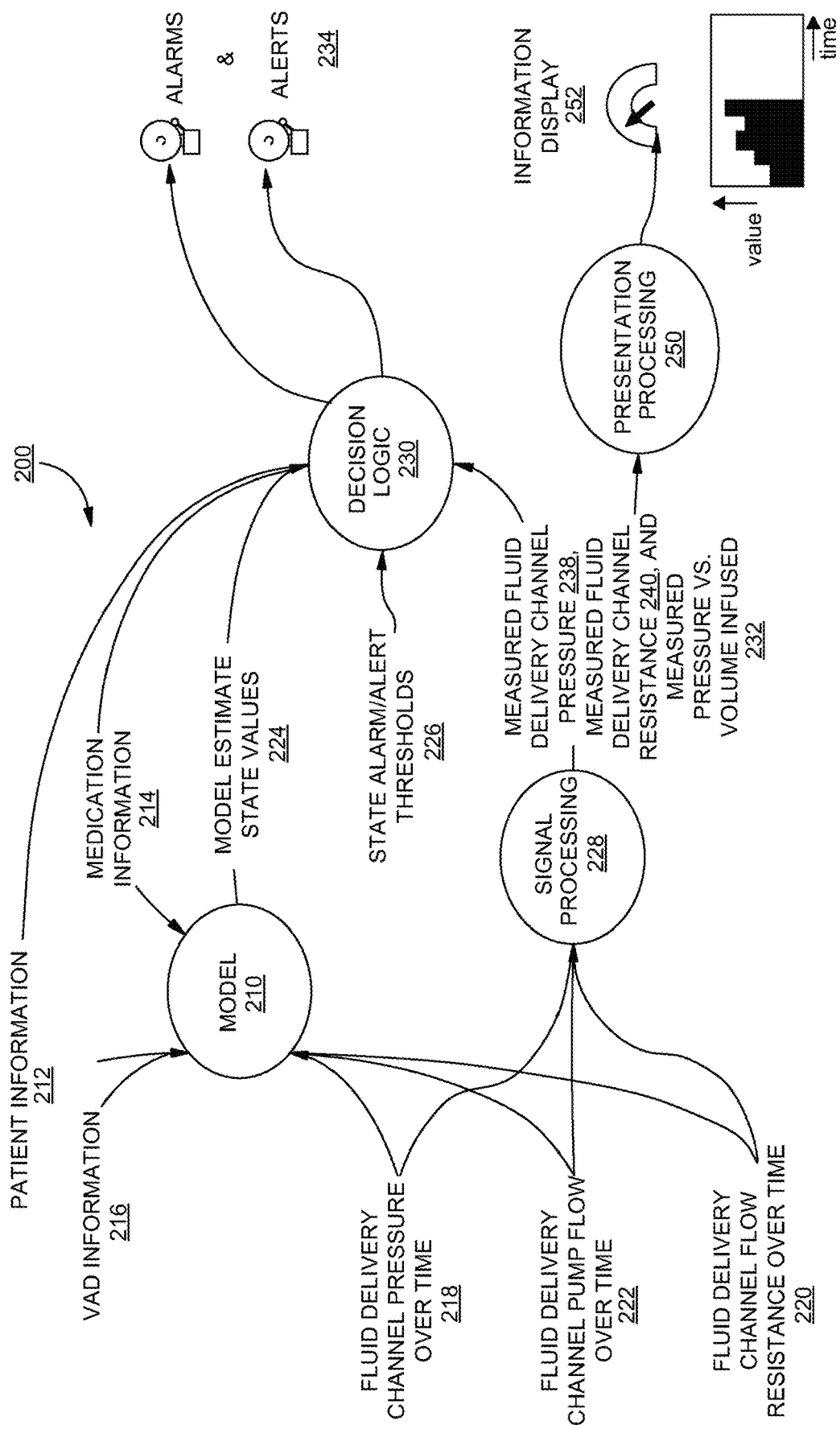
FIG. 2 is a state diagram of the medication delivery monitoring system of FIG. 1.

FIG. 2 is a signal flow and processing high level state diagram 200 of the medication delivery monitoring system of FIG. 1. The model 210, generated by processor 106, is based on various inputs, including, for example, patient information 212 (e.g., weight and other non-varying attributes), fluid delivery channel pump flow 222 of the medication 118 over time, fluid delivery channel (e.g., IV line) pressure 218 over time (e.g., with reference to the history of recorded values of measured fluid delivery channel pressure, which is stored in memory 120), fluid delivery channel resistance 220 over time, and VAD information 216. In certain embodiments, the model 210 is also based on an input that includes medication information 214. The fluid delivery channel pump flow 222 of the medication 118 over time, fluid delivery channel pressure 218 over time, fluid delivery channel resistance 220 over time, and VAD information 216 is also provided for signal processing 228, such as by processor 106. The output of the model 210, including estimated state values 224 of the infusion site region 114 of the patient 116 (e.g., how much infused fluid has infiltrated the infusion site region 114, or protein, a critical factor in fluid transport between the vasculature, lymph and ITS, is in the infusion site region 114), is provided to decision logic 230 (e.g., in processor 106) for processing with, for example, a currently measured fluid delivery channel pressure 238, a currently measured fluid delivery channel resistance 240, and a currently measured pressure versus volume infused 232. These currently measured values 238, 240, and 232 are provided by the signal processing 228, and are further provided for presentation processing 250, including possible scaling and offset smoothing range dynamics, to optionally be displayed on an information display 252, such as the output device 108. For example, the expected pressure and resistance 224 of the fluid delivery channel 110 and the currently measured fluid delivery channel pressure 238 and resistance 240 can be displayed to an operator for monitoring the infusion of the medication 118 to the patient 116. Returning to the decision logic 230, if the currently measured values 238, 240, and 232 and the model estimate values 224 indicate that the infusion site region 114 has been infiltrated, as based on provided state alarm and alert thresholds 216, which may be functions of the patient information 212 and the medication information 224, then an alarm and/or alert 234 is indicated, by, for example, the output device 108, or, in certain embodiments, a control 234 of the medication infusion to the patient 116 is adjusted, such as by the pump associated with the medication delivery monitoring device 100.

Figure 3A:
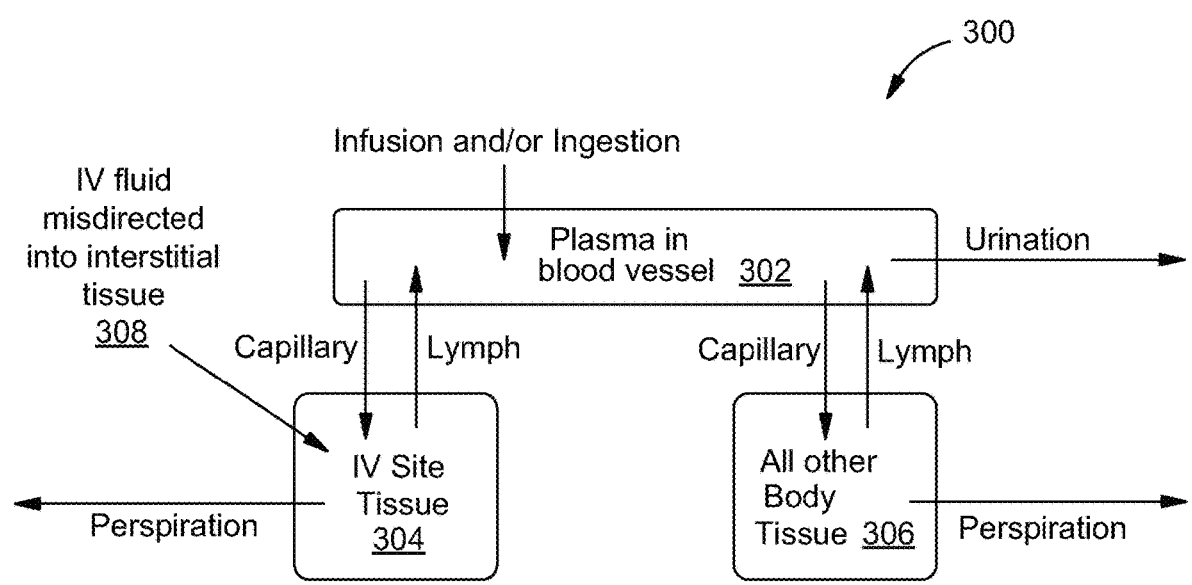
FIG. 3A is an exemplary three-compartment model of an infusion site region of a patient.

FIG. 3A is an exemplary compartment model 300 of an infusion site region 114 of a patient 116. As shown in FIG. 3A, a generalized and highly simplified example, a compartment model divides the body's fluid into discrete homogeneous compartments: plasma (within the blood vessel) 302, IV site immediate tissue 304 (in which IV fluid may be misdirected), and all other body tissue 306 (i.e., all regions outside the immediate field of the IV site). The model calculates the fluid volume and protein mass (a primary influence on fluid transport between compartments) within each of these compartments 302, 304, and 306 over the course of a simulated infiltration based on controlled flow from the pump and measured pressures as well as properties of the tissue estimated from user inputs describing the site and patient age/weight. An increase in fluid volume (e.g., the sum of blood plasma and IV fluid) within the interstitial space is a primary indicator of a growing complication likely due to misplacement of the vascular access device.

The expressions for fluid and protein transport are described by six ordinary differential equations, as described in further detail below. Pressure in the immediate IV site region tissue compartment is calculated from a pressure-volume (compliance) curve derived from patient weight and site description because the weight and site is known. This type of model describes the transport of fluid and protein between each compartment using ordinary differential equations (ODEs). This transport of fluid and protein is a result of the microvascular exchange system. A more sophisticated model includes lymph drainage and an exogenous, time-dependent fluid input 308 as would occur during an infiltration or deliberate subcutaneous injection. This more sophisticated model allows the average pressure and total volume of fluid in each compartment to be calculated. Because each compartment is assumed to be homogeneous this model does not show fluid movement internal to the compartment. However, compartment models described by ODEs are simpler than continuum models, and therefore are easier to define and faster to solve. Compartment models have been used with great success in the field of pharmacokinetics.

To explain in more detail how the compartment model was developed for this application, two exemplary, simplified embodiments of a compartment model will now be described in greater detail. Compartment models (or lumped element models) predict quantities and rates of change (e.g., transport) of a substance in different compartments. First, a two compartment model, FIG. 3B, which considers the circulatory system (plasma) and the rest of the tissue (interstitial tissue space) is described. Then the model is extended to a three-compartment system, incorporating a local compartment that describes fluid near the infusion site.

Figure 3B:
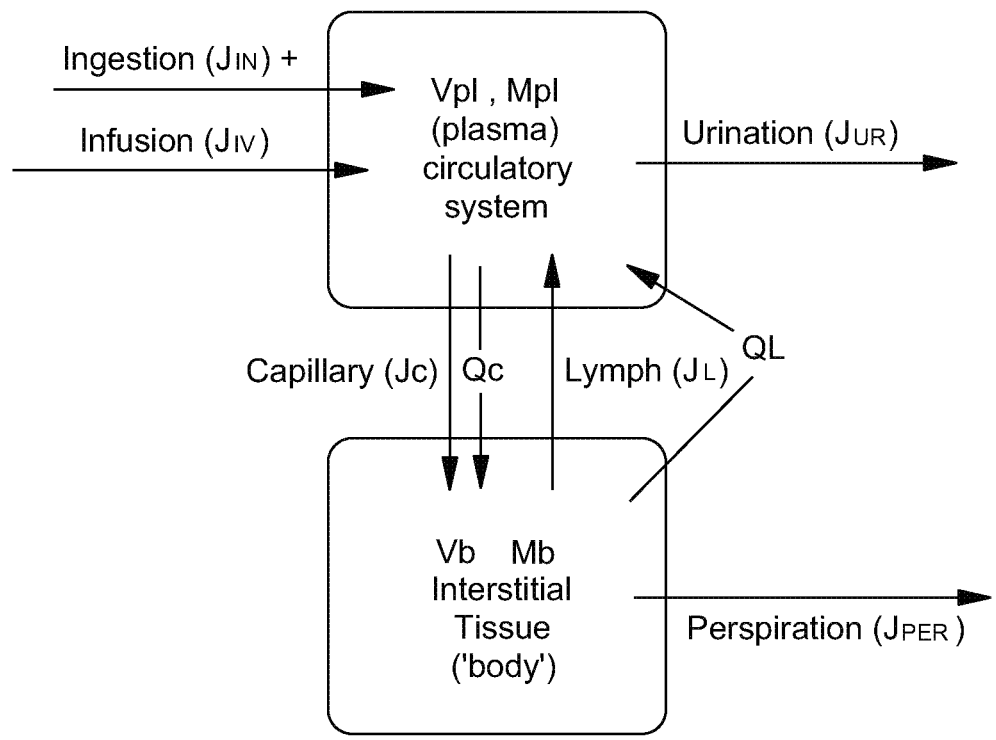
FIG. 3B is an exemplary two-compartment model of an infusion site region of a patient.

A simplified, two-compartment model is first considered that divides the body's fluid into two homogeneous compartments, the plasma (PL) and interstitial (body) tissue (B), as seen in FIG. 3B. This model estimates the volume of fluid, V, and protein mass, M, in both compartments. The fluid volume of the plasma and body tissue is denoted as $V_{PL}$ and $V_B$, and the protein mass in each compartment as $M_{PL}$ and $M_B$. In a more complete model to be described following this model, a source of exogenous fluid and protein will be added to the plasma compartment simulating a normally placed VAD, or to the interstitial tissue simulating an infiltrated condition.

In the simplified model shown in FIG. 3B, the transport of fluid, i.e. the time rate of change of its volume, $dV_B/dt$, and protein, $dM_B/dt$, into the interstitial tissue is defined as the difference between transport across the capillary membrane into the tissue, $J_C$ and $Q_C$, and the lymph transport out of the tissue into the plasma, $J_L$ and $Q_L$, as well as fluid loss via perspiration from the circulatory system, $J_{per}$:

$$dV_B/dt = J_C - J_L - J_{per}, \quad (2.1)$$

and $$dM_B/dt = Q_C - Q_L. \quad (2.1)$$

Net transport (i.e. time rate of change of fluid and protein) into the plasma are given by the difference between lymph flow $J_L$ and capillary flow $J_C$, with additional fluid input from ingestion, $J_{in}$, and infusion, $J_{iv}$, and loss due to urination, $J_{ur}$:

$$dV_{PL}/dt = J_L - J_C + J_{in} + J_{iv} - J_{ur}. \quad (2.3)$$

and $$dM_{PL}/dt = -dM_B/dt = Q_L - Q_C \quad (2.4)$$

Fluid exchange occurs across the capillary membranes (from vessel (PL) to interstitial tissue (B)) is modeled according to Starling's Law of membrane filtration, $$J_C = \kappa[(P_{PL} - P_B) - \sigma(\Pi_{PL} - \Pi_B)] \quad (2.5)$$

In Starling's Law, fluid flow is driven by two mechanisms. First, Darcy's Law states that flow through a porous medium (here, the capillary membrane that separates the arterial and venous blood vessels from the surrounding interstitial tissue) is proportional to the difference in fluid hydrostatic pressure ($\Delta P = P_{PL} - P_B$). Second, fluid flow follows an osmotic gradient ($\Delta \Pi = \Pi_{PL} - \Pi_B$) caused by differences in protein concentration across the capillary membrane as described by Equations 2.6 and 2.7.

Proteins are considered because they are the most important solutes affecting fluid transport between the circulation and body tissue. This is due to protein's low diffusivity compared to smaller solutes, such as ions. Any difference in protein concentration between compartments causes a colloid osmotic pressure gradient, $\Delta \Pi$, that affects fluid flow across the capillary membrane according to Starling's Law (see Equation 2.5). The relationship between protein concentration, C, and colloid osmotic pressure, $\Pi$, in each compartment is given as $$C_{PL} = 1.522 \cdot \Pi_{PL} \quad (2.6)$$

$$C_B = 1.522 \cdot \Pi_B \quad (2.7)$$

The value 1.522 is derived from a linear regression fit to pressure-concentration data. The osmotic effects of small solutes are ignored because their effect on fluid flow is generally less significant.

The magnitude of transport (e.g., flow) due to the osmotic gradient depends upon the reflection coefficient ($\sigma$) of the solute, which is a measure of the solute's diffusivity. Solutes that readily diffuse across the membrane have less impact on fluid flow (smaller $\sigma$ values, approaching 0), while solutes that can barely diffuse have more impact on fluid flow across the capillary membranes (larger $\sigma$ values, approaching 1). According to one embodiment, in the disclosed model, protein has a high $\sigma$ value (0.96-0.99), while ions would have much lower $\sigma$ values (on the order of 0.05). For this reason the osmotic effects of ions are not included. The capillary fluid filtration coefficient ($\kappa$) is an experimentally determined constant which affects the transport rate of both proteins and fluid. The value $\kappa = 121.1$ mL/mmHg·hr is used.

Protein transport across a membrane is described by both convection and diffusion according to the following formula:

$$Q_C = -p \frac{dC}{dx} + C_{PL}(1 - \sigma)J_C \quad (2.8)$$

Protein diffuses proportionally (according to the membrane permeability, $P_m$, at constant volume) to the concentration gradient $$\left( \frac{dC}{dx} \right).$$

Figure 3C:
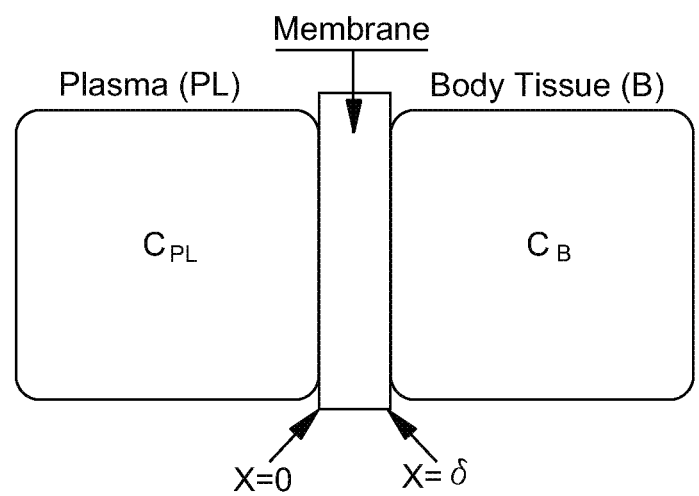
FIG. 3C is a diagram illustrating how Equation 2.9 is derived from Equation 2.8.

Protein is carried across the membrane via convection proportionally to both capillary fluid flow ($J_C$) and the concentration of protein in the plasma ($C_{PL}$). Reflection coefficient $\sigma$, described above, is a measure of the protein's diffusivity and small values correspond to readily diffusive solutes. Thus, $(1-\sigma)$ will be near 1 for readily diffusive solutes (ions) and near 0 for less diffusive solutes (proteins). The capillary permeability surface area product, $\mu$, is equal to $P_m/\delta$, and is a measure of the membrane permeability per unit area. The surface area product, $\mu$, can be thought of as the amount of plasma volume that gives up its solute contents to the interstitial fluid per unit time (on the order of 73 mL/hr). Equation 2.8 is a first order linear differential equation for $C(x)$ where $C(0) = C_{PL}$ and $C(\delta) = C_B$. Integrating along the x-axis (across the membrane from $x=0$ to $x=\delta$, see FIG. 3C) using the integrating factor $e^{-x(1-\sigma)J_C/\mu}$ leads to the following expression for protein transport across capillaries ($Q_C$):

$$Q_C = (1-\sigma)J_C \left[ \frac{CPL - CB \cdot e^{\frac{-(1-\sigma)J_C}{\mu}}}{1 - e^{\frac{-(1-\sigma)J_C}{\mu}}} \right] \quad (2.9)$$

Fluid is transported through the lymph from the interstitial tissue back to the plasma, $$J_L = J_{L0} + \lambda(P_B - P_{B0}) \quad (2.10)$$

Lymph fluid flow is described in Equation 2.10 as a basal lymph flow rate ($J_{L0}$) plus a term proportional to the deviation from normal interstitial fluid pressure ($P_B - P_{B0}$). The proportionality constant is the lymph sensitivity ($\lambda$) to changes in pressure, which is on the order of 43.1 mL/mmHg·hr.

Protein is removed from the interstitium and travels back to the plasma via the lymph flow, which is assumed to be convective and proportional to the interstitial protein concentration ($C_B$), $$Q_L = J_L \cdot C_B \quad (2.11)$$

No protein is assumed to be lost from the system. However, the model includes several sources of fluid loss: insensible water loss (which occurs through membranes, primarily the lungs), perspiration, and urination. Insensible loss is modeled as constant fluid outflow because water leaves from the wet mucous membranes of the lung as a necessary consequence of breathing. The expected impact of systemic water loss from the entire circulatory system on the regional modeling of infiltration is small, yet this term is employed for completeness.

Figure 3D:
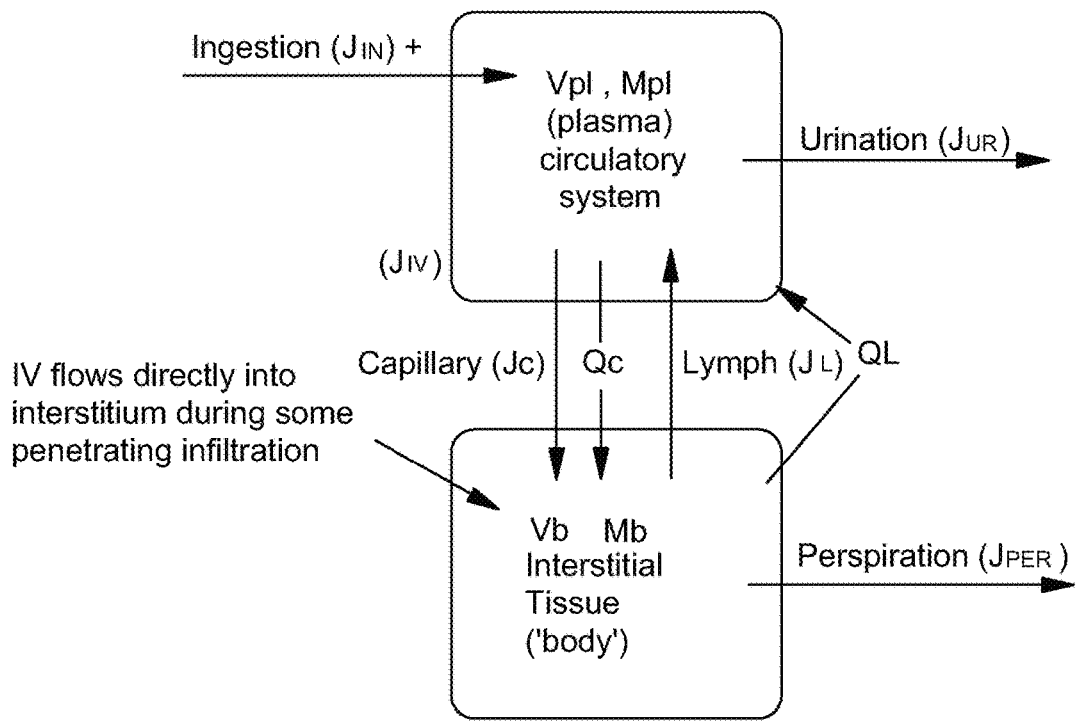
FIG. 3D is a diagram of an infiltration in the two-compartment model of FIG. 3B.

To model an IV infiltration, the IV input ("infusion") is "moved" from the vein (FIG. 3B) to the interstitial tissue compartment (FIG. 3D). FIG. 3D models an IV needle puncturing the vein and infusing fluid into the surrounding interstitial tissue.

Figure 3E:
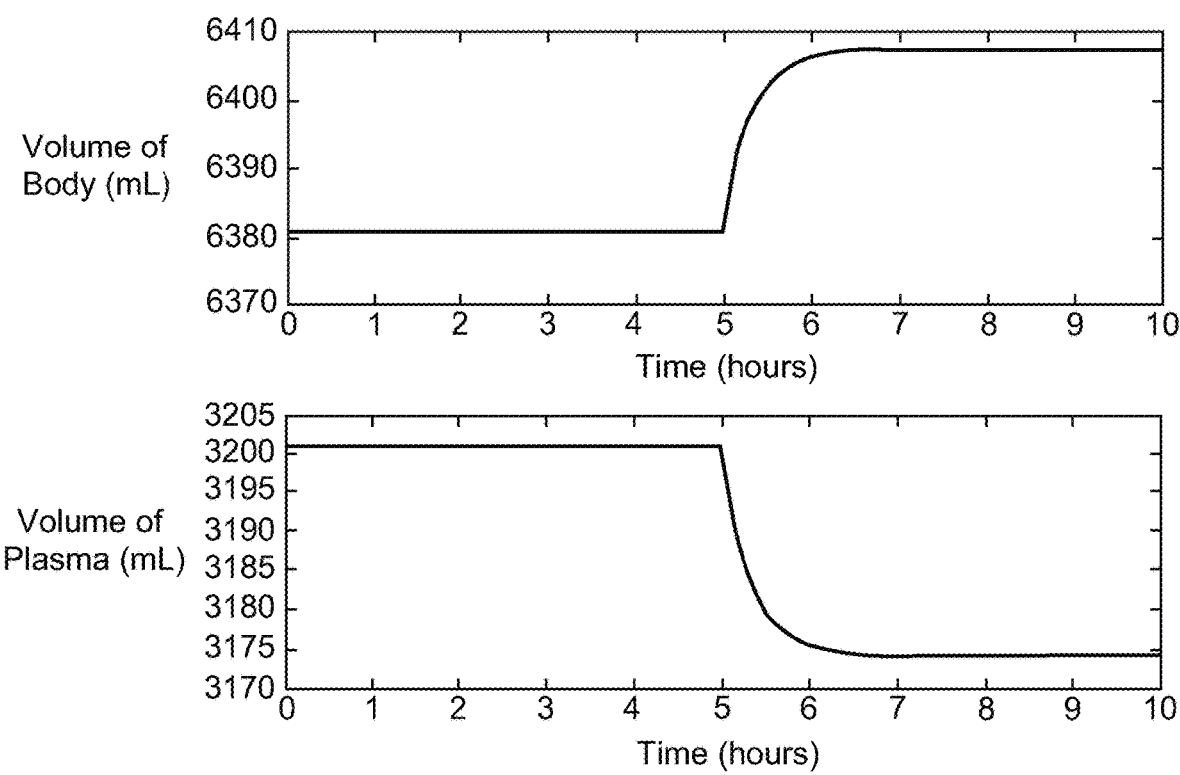
FIG. 3E is a modeling of an infiltration.

Fluid is not cleared from the body tissue by the lymph vessels and perspiration ($J_L$, and Jper) as quickly as fluid enters from the plasma by the capillaries ($J_C$) and from the infiltrated IV needle ($J_{in}$), fluid builds up in the interstitium when the IV fluid input is moved from the vein to the interstitium (FIG. 3E). An example simulation is shown in FIG. 3E, where fluid is infused at a rate of 100 mL/hr into the bloodstream for the first 5 hours. At time t=5 hours the fluid input is moved to the body tissue compartment, simulating an infiltration. By time t=7 hours the body interstitial fluid volume reaches a new steady state volume, 24 mL, above the original steady state volume during normal infusion into the bloodstream.

The above simplified, two-compartment model treats all of the interstitial tissue in the entire body as one compartment. However, fluid volume changes in the vicinity of the injection site are described more accurately by using a local interstitial compartment separate from the rest of the body. Fluid movement away from an infiltrated site can occur principally by diffusion through the interstitial tissue matrix and by flow through the lymph vessels.

Figure 3F:
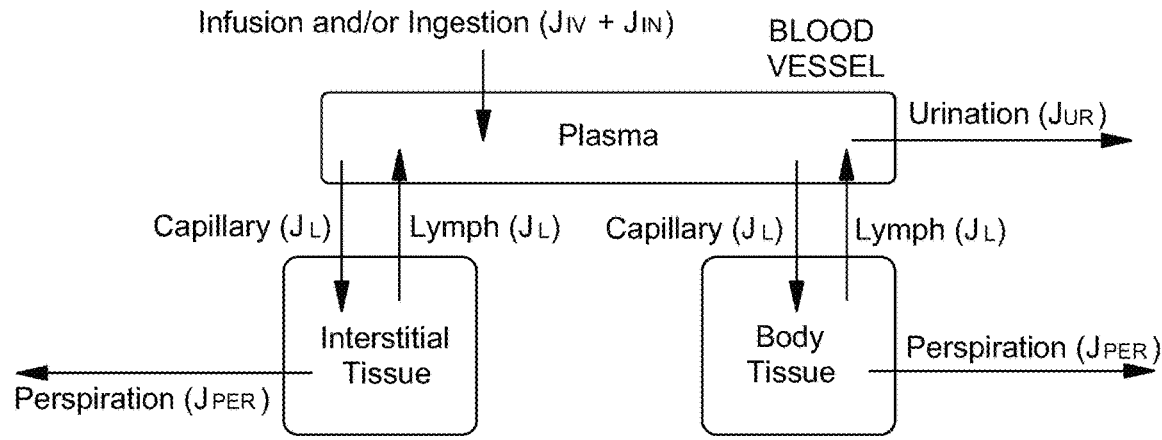
FIG. 3F is an exemplary three-compartment model of an infusion site region of a patient.

To provide a better approximation of the actual anatomy, the original interstitial tissue compartment is replaced by two compartments: an arm (A) interstitial tissue and a body (B) compartment. In FIG. 3F, fluid enters the system by infusion into a third compartment, the blood vessel containing plasma. Fluid leaves the system by both urination from the plasma and perspiration from the interstitium through the skin. Plasma exchanges its fluid component with the tissue compartments through capillary and lymph vessels. With a model of this complexity, fluid movement between tissue compartments is considered insignificant relative to vessel-tissue movement. The fluid volume of the arm tissue/immediate IV site region tissue compartment is denoted as $V_A$ and the protein mass of the arm interstitium compartment as $M_A$. The fluid volume and protein mass of the body tissue compartment become $V_B$ and $M_B$. A local/arm vessel/plasma compartment is unnecessary because the plasma fluid flow rate between vessels in the arm and plasma elsewhere in the body is so much faster than fluid flow between plasma and tissue that it can be approximated as instantaneous.

To extend the two-compartment model to the three-compartment model, the same basic equations are used and modified to reflect the different sizes of the two tissue compartments. A new parameter, prop, is defined to be the proportion of the arm interstitial volume in the region of an IV site to be modeled compared to the total interstitial volume. Initially, prop=1.5/70, as the average weight of an adult human forearm is around 1.5 kg and the subject considered weighs 70 kg.

The prop parameter can be thought of as the proportion of capillary and lymph vessels servicing the local/arm compartment. Since the arm is 1/40 of the body, then using simple proportioning, approximately 1/40 of the body's capillary and lymph vessels may be available to move fluid between the plasma and the arm interstitial tissue compartment. The other 68.5/70 of the capillary and lymph vessels move fluid between the plasma and the body interstitium compartment. Consequently, the fluid transport for a given pressure difference will be scaled to the compartment size.

The capillary permeability surface area product, $\mu$, is scaled by prop for the arm interstitium compartment and (1−prop) for the body interstitium compartment (recall that $\mu$ is permeability divided by membrane thickness ($\mu = p/\delta$)). Intuitively this makes sense because the number and surface area of in each tissue compartment is scaled down.

In the three-compartment model, the transport of fluid and protein depends on two separate lymph and capillary flow rates for each interstitial tissue compartment. Equation (2.5) that describes fluid transport across capillaries is scaled by prop to become the equation for fluid flow across the capillaries to the arm compartment:

$$J_{CA} = \text{prop} \cdot \kappa[(P_{PL} - P_A) - \sigma(\Pi_{PL} - \Pi_A)] \quad (2.12)$$

and fluid transport across the capillaries to the body compartment becomes:

$$J_{CB} = (1-\text{prop})\kappa[(P_{PL} - P_B) - \sigma(\Pi_{PL} - \Pi_A)] \quad (2.12)$$

The equation for fluid transport from the interstitium to the plasma through the lymph (Equation 2.10) is similarly scaled by prop for the arm compartment:

$$J_{LA} = \text{prop}(J_{L0} + \lambda(P_A - P_{A0})) \quad (2.14)$$

and (1−prop) for the body compartment:

$$J_{LB} = (1-\text{prop})(J_{L0} + \lambda(P_B - P_{B0})) \quad (2.15)$$

Under non-infiltrated conditions, both arm and body interstitial compartments are assumed to have the same normal hydrostatic pressure (i.e., $P_{B0} = P_{A0}$) when the patient is supine.

The equations for both capillary and lymph protein transport do not need to be explicitly scaled by prop because they contain the expressions for fluid flow ($J_{CA}$ and $J_{CB}$), which have already been scaled. Thus, the modified capillary protein transport equations are (compare with Equation 2.9, note the subscripts denote source-destination of the movement e.g. "CA" means capillary to arm[interstitial tissue] and "CB" denotes capillary to body):

$$Q_{CA} = (1-\sigma)J_{CA}\left[\frac{C_{PL} - C_A \cdot e^{\frac{-(1-\sigma)J_C}{\mu \cdot prop}}}{1 - e^{\frac{-(1-\sigma)J_C}{\mu \cdot prop}}}\right] \quad (2.16)$$

and $$Q_{CB} = (1-\sigma)J_{CB}\left[\frac{C_{PL} - C_B \cdot e^{\frac{-(1-\sigma)J_C}{\mu \cdot prop}}}{1 - e^{\frac{-(1-\sigma)J_C}{\mu \cdot prop}}}\right] \quad (2.17)$$

The lymph protein transport equations are now (compare with Equation 2.11):

$$Q_{LA} = J_{LA} \cdot C_A \quad (2.18)$$

and $$Q_{LB} = J_{LB} \cdot C_B \quad (2.19)$$

Figure 3G:
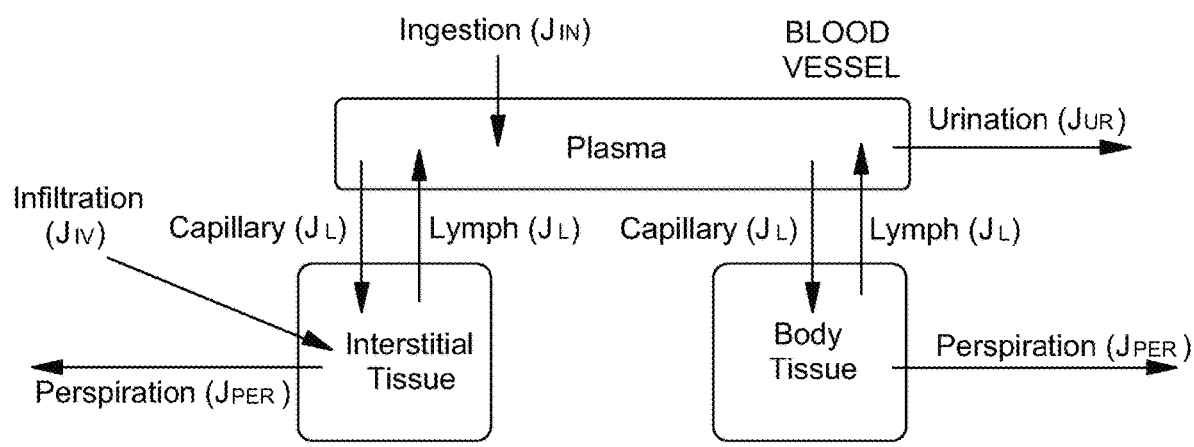
FIG. 3G is a diagram of an infiltration in the three-compartment model of FIG. 3F.

To model an IV infiltration, the IV input ($J_{iv}$) is moved from the plasma to the immediate IV site region/arm tissue compartment (FIG. 3G). For the adult case, to replace body fluids, thereby holding local peripheral venous pressure relatively constant, the sum of inward flows ($J_{in}+J_{iv}$) is assumed constant at 100 mL/hr, and balanced by the urination term resulting in typical peripheral venous pressures of 0 to 10 mmHg in a supine position. This models an IV needle accidentally puncturing the vein, infusing fluid into the surrounding interstitial tissue, but not into interstitial tissue far away from the injection site.

FIG. 3H summarizes the complete set of model equations. Estimates of parameters for a normal, reclining 70 kg adult can be found in FIG. 3I. In FIG. 3I, interstitium parameters (indexed by I) apply to both the body interstitium and arm interstitium compartments, with the body interstitium versions being scaled by (1−prop) and the arm interstitium versions scaled by prop.

Figure 3J:
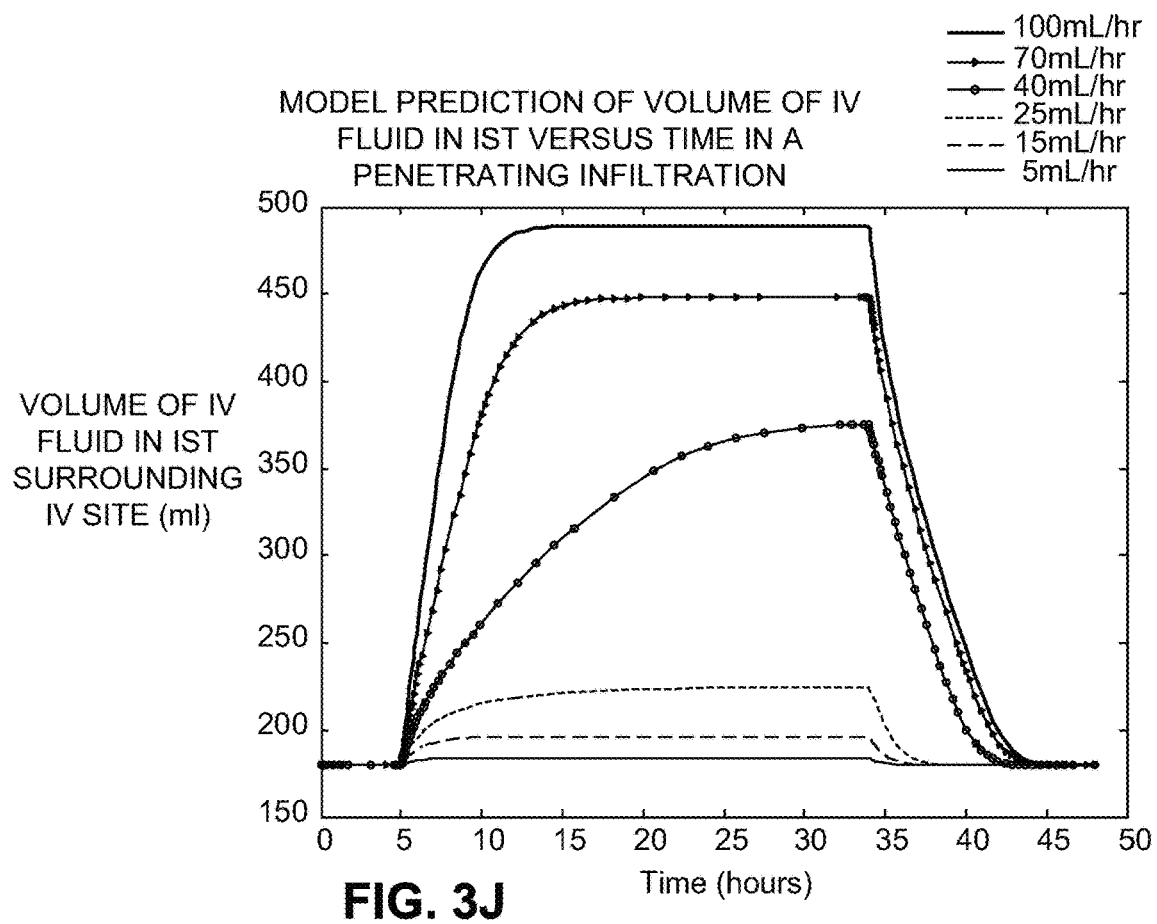
FIG. 3J illustrates model prediction of volume in the tissue near the site of an infusion.

Behavior of infiltrations in the arm (antecubital site) in adults for typical infusion rates up to 100 mL/hr is now considered. With infusion rates below 15 mL/hr, the volume of fluid in the interstitial tissue surrounding the cannulation site is estimated to increase by less than 10 percent during infiltration. FIG. 3J illustrates model prediction of volume in the tissue near the site of an infusion. Fluid is shown infused at various rates into the plasma until time t=5 hours. Next, the VAD "infiltrates" the tissue, resulting in the local infusion site region volume increasing toward a steady state level. The steady state is achieved since the accompanying increased pressure forces fluid out through the lymph and the surrounding tissue until equilibrium is reached. At time t=34 hours, the infiltration is removed and the infusion into the plasma resumes, the excess fluid in the infusion site region diminishes toward normal at a rate somewhat proportional to the peak volume.

Figure 3K:
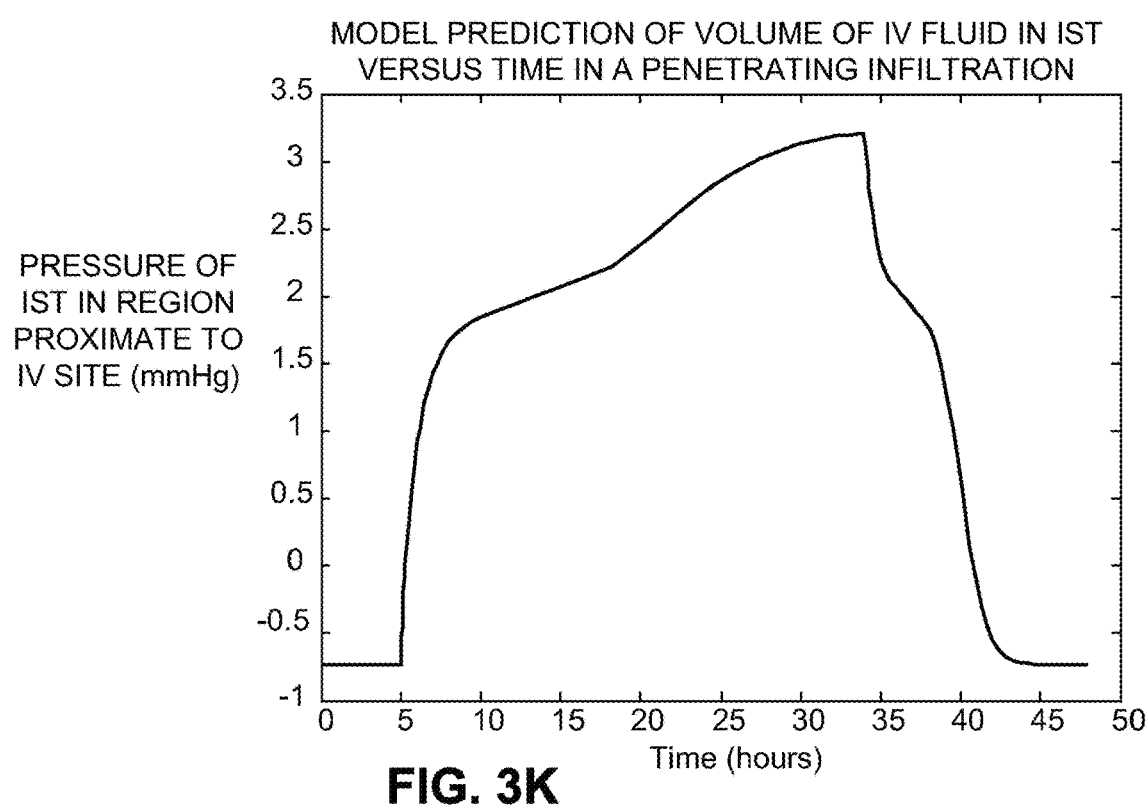
FIG. 3K illustrates a measurement of pressure in the tissue near the site of an infiltration over time.

At most rates, pressure increases nonlinearly because of the relationship between the infusion site region's volume and pressure. The normal arm tissue hydrostatic pressure is −0.7 mmHg in the supine adult. The three compartment model estimates pressure in the arm tissue in ranges from about −0.4 mmHg with an infusion of 5 mL/hr to about 17 mmHg with an infusion of 100 mL/hr. At 40 mL/hr, the pressure increases to 3.2 mmHg within 30 hours of infiltration (FIG. 3K). FIG. 3K illustrates pressure in the interstitial tissue near the site of an infiltration. Fluid is being infused at 40 mL/hr into the vein until time t=5 hours. Then, the needle infiltrates the tissue and the interstitial tissue pressure increases. The increase is nonlinear because the tissue compliance is nonlinear (the tissue can stretch to a maximum after which a small increase in volume greatly increases pressure). At time t=34 hours, the infiltration is removed and the 40 mL/hr infusion into the vein resumes. Like volume, pressure dissipates more rapidly than it built up. These volumes and pressures are averages for the compartments. FIG. 3K uses 1.5/70 as the proportion and showed pressure response to infiltration at various infusion rates.

Figure 3L:
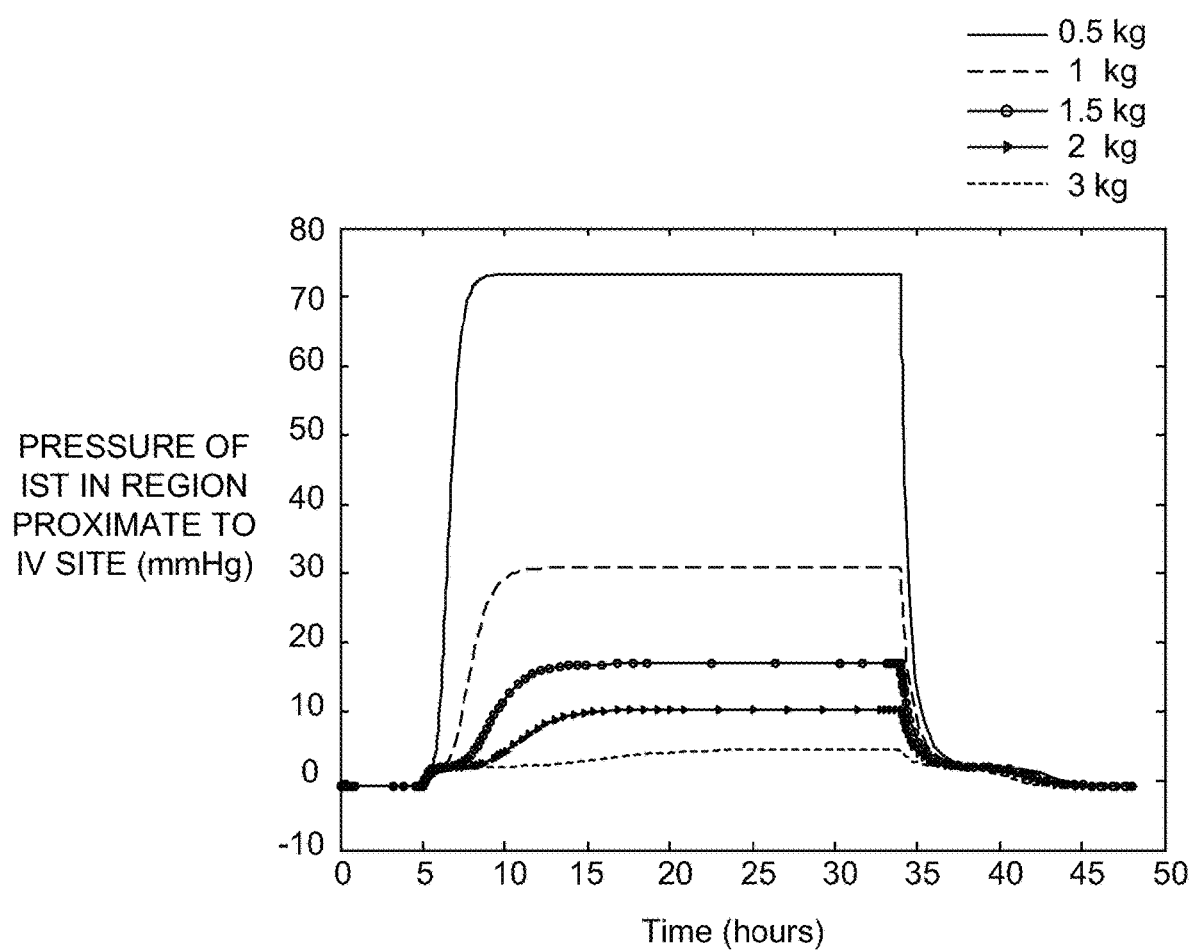
FIG. 3L illustrates a measurement of pressure in immediate IV site region tissue compartments of various sizes over time.

FIG. 3L illustrates the model prediction of the pressure response to infiltration at 100 mL/hr as plotted in arm compartments of different sizes. Intravenous fluid is being infused at 100 mL/hr into the vein until time t=5 hours. Then, the VAD infiltrates the tissue resulting in the interstitial tissue pressure increasing. Smaller compartments show greater maximum pressure, revealing pressure changes close to the injection site. At time t=34 hours, the in the pump flow is returned to the vein. With an antecubital arm compartment of 0.5 kg (for a 70 kg adult), the pressure during infiltration is greater than 70 mmHg. One previous study found that the average pressure at the injection site during 100 mL/hr infiltration ranges from about 0.5 mmHg to about 2 mmHg for each mL/h.

Figure 4A:
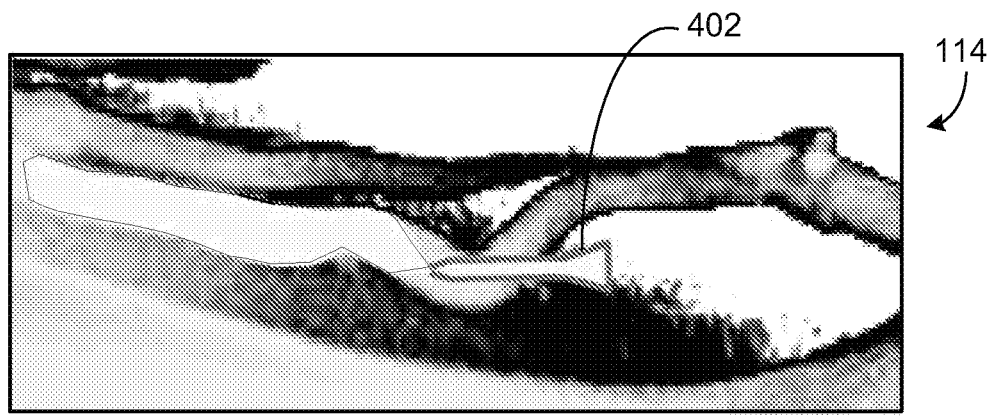
FIGS. 4A-4C illustrate three positions of a vascular access device for an exemplary continuum model of an infusion site region of a patient.
Figure 4B:
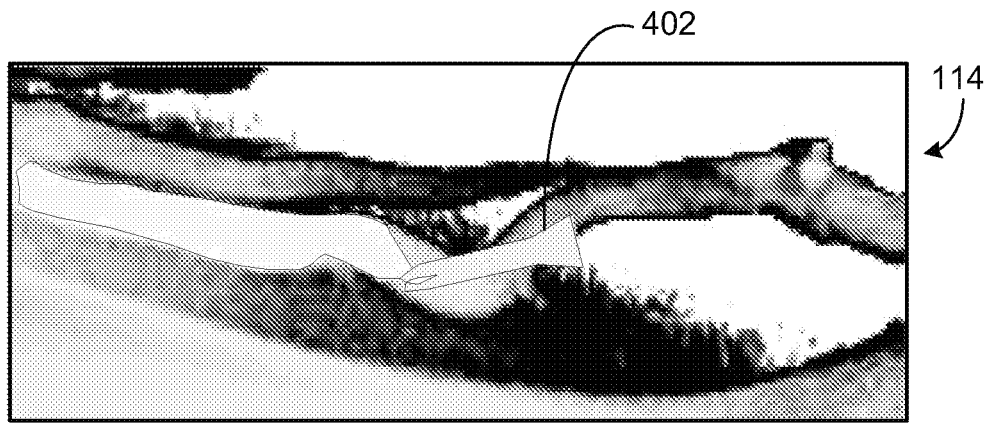
Figure 4C:
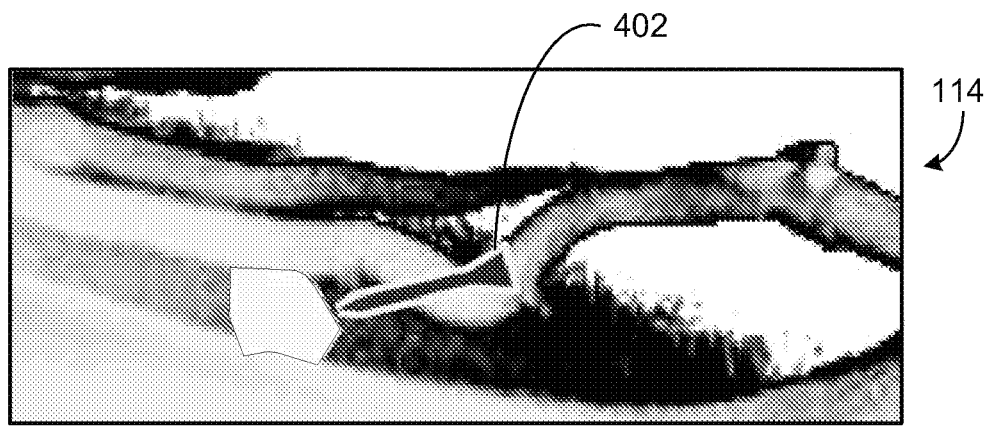

Having detailed the compartment model, FIGS. 4A-4C illustrate three positions of a vascular access device for an exemplary continuum model 400 of an infusion site region 114 of a patient. Specifically, FIG. 4A illustrates an etiology of infiltration/extravasation of a cannula 402 in a vein, FIG. 4B illustrates an etiology of infiltration/extravasation of a positional cannula 402, and FIG. 4A illustrates an etiology of infiltration/extravasation of a cannula 402 that has penetrated into interstitium tissue, resulting in an infiltration. If, in FIG. 4C, the fluid delivered by the cannula were toxic, the condition would be defined as an extravasation. The continuum model can be used to corroborate the predictive ability of the discrete compartment model, and to obtain insight into the behavior of the infiltrated infused fluid with the media of the interstitial space. Current real-time battery operated processors are not yet able to provide this level of computation for direct application, however the growing use of wireless connected servers might make performing such computations for a large number of pumps in near real time feasible in the future.

A continuum model 400 describes an infiltration by considering the injected fluid's motion from the injection site and its interactions with a region of surrounding tissue. Two coupled partial differential equations model a poroelastic tissue using Darcy's Law and a solid deformation equation, as described in further detail below. In certain embodiments, an ideal continuum model is a more appropriate type of model in that it could exactly describe the motion of the injected medication in three dimensions. In certain embodiments, a continuum model must realistically include simplifications due to a limited knowledge of the tissue properties, initial conditions, and boundary conditions. In addition, continuum models are represented mathematically by partial differential equations, which are usually not solvable in closed-form; instead, a computer-based numerical solver is used to find solutions. A simplified model of fluid flow in tissue is described by Darcy's Law of flow through porous media in which the local flow rate is proportional to the pressure gradient. Fluid flow in biological tissue is often modeled using theories of porous media flow in which a fluid is restricted to move through small pores in a solid medium. Poroelastic models are more complicated models in which the porous medium has elastic properties. The porosity depends not just on the position in a material, but also on the properties of the fluid flow. One motivation for a poroelastic model is that the properties of the interstitial tissue can change dramatically depending on the presence or absence of added fluid: one study reports that the hydraulic conductivity can change by a factor of 250,000 during an infiltration. The continuum model is based on the theory of poroelasticity and is described by two coupled partial differential equations (PDEs).

A continuum model, as opposed to a compartment model, describes the motion of an injected fluid and its interactions with a region of surrounding tissue. The continuum model provides information (such as pressure or velocity) at every point in the region and at every instance of time. Mathematically, a continuum model is described using a system of PDEs.

The Navier-Stokes equations are a common continuum model which describe flow of a single fluid, for example, water flowing through a metal pipe. In the case of fluid flow in biological tissue, the Navier-Stokes model is insufficient because it fails to account for the solid structure (collagen and elastin) present throughout the tissue. A more appropriate model is based on the empirically-derived Darcy's Law, which describes low-speed fluid flow through a porous medium, such as groundwater through soil. Darcy's Law alone does not model the compliance or elasticity of the tissue, so it cannot predict phenomena such as swelling from edema. In order to account for deformation of the tissue, Darcy's Law is applied in combination with an elastic deformation model. The combination, called poroelasticity, describes a solid elastic matrix through which a pure fluid may flow. The fluid flow and deformation models are coupled so flow induces deformations, while deformations in turn affect the fluid flow. Poroelasticity is commonly used as a model for fluid flow through biological tissue. In certain embodiments, an alternative model called mixture theory can be used to describe fluid flow in biological tissue.

In certain embodiments, the poroelastic model is implemented in COMSOL Multiphysics, a software package designed to numerically solve continuous physical problems. Poroelasticity is included as a predefined "Multiphysics" mode in COMSOL, although some modifications can improve the relevance of the model to the problem. The following sections describe the governing equations, parameters and boundary conditions used to model both the fluid flow and elastic deformation, as well as the results from the disclosed model.

The poroelastic model is described by two coupled partial differential equations. The first equation governs the fluid flow through the tissue and is based on Darcy's Law. Darcy's law is an empirically derived statement that relates fluid flow to the pressure gradient. It assumes a low flow rate and can also be derived from the Navier-Stokes Equations using several simplifying assumptions. Darcy's Law states $$q = -\frac{K}{\rho_f g}\nabla p \quad (3.1)$$

where q is the discharge of fluid per unit area (flux), K is the hydraulic conductivity, $\rho_f$ is the fluid density, g is the gravitational acceleration, and p is the fluid pressure.

Equation (3.1) is used in conjunction with a continuity equation to derive the fluid flow governing equation in the poroelastic model. The continuity equation states that the rate at which fluid mass enters a region is equal to the rate at which mass leaves a region. This can be expressed as $$\frac{\partial(\rho_f \theta_s)}{\partial t} + \nabla \cdot \rho_f q = \rho_f Q_{source} \quad (3.2)$$

where $\theta_s$ is the fraction of the volume available for fluid flow and $Q_{source}$ is the strength of a fluid source or sink (1/s) within the region itself. Substituting in the equation for flux from Eq. (3.1) into Eq. (3.2) yields $$\frac{\partial(\rho_f \theta_s)}{\partial t} + \nabla \cdot \left[\rho_f \left(\frac{-K}{\rho_f g}\nabla p\right)\right] = \rho_f Q_{source}$$

For an incompressible fluid $\rho_f$ is constant and can move outside the divergence operator. Dividing through by $\rho_f$ gives us $$\frac{\partial \theta_s}{\partial t} + \nabla \cdot \left(\frac{-K}{\rho_f g}\nabla p\right) = Q_{source}$$

In the disclosed model, the ability of the solid structure to expand and contract is analogous to pressure sources or sinks. If the solid expands, the pressure in the region will decrease assuming no additional fluid enters the region. Similarly, if the solid contracts, the pressure increases, acting as a pressure source. This is expressed by letting $$Q_{source} = -\alpha_b \frac{\partial e}{\partial t}$$

where $\partial e/\partial t$ is the time rate of change of volumetric dilation (s$^{-1}$) from the equation for the elastic deformation and $\alpha_b$ is an empirical constant called the Biot-Willis coefficient. The resulting governing equation is $$\frac{\partial \theta_s}{\partial t} + \nabla \cdot \left(\frac{-K}{\rho_f g}\nabla p\right) = -\alpha_b \frac{\partial e}{\partial t}. \quad (3.3)$$

The equation can be simplified by using the chain rule to define $$S_a = \rho_f g \left(\frac{\partial \theta_s}{\partial p}\right)\left(\frac{\partial p}{\partial t}\right)$$

as the storage coefficient (m$^{-1}$). The storage coefficient is typically found experimentally, and it can be defined either in units of m$^{-1}$, used here, or Pa$^{-1}$. The difference between the two definitions is a factor of $\rho_f g$. The equation implemented in the continuum model is $$\left(\frac{S_a}{\rho_f g}\right)\frac{\partial p}{\partial t} + \nabla \cdot \left(\frac{-K}{\rho_f g}\nabla p\right) = -\alpha_b \frac{\partial e}{\partial t}.$$

In the disclosed model the empirically derived value $\alpha_b t = 1$ is used for the Biot-Willis coefficient. The value for hydraulic conductivity is set to $K=10^{-7}$ m/s, which is a typical value found experimentally for the subcutaneous tissue of rats. The storage coefficient, Ss, is set to $10^{-8}$ m$^{-1}$. The fluid is assumed to be mostly water, therefore the density is $\rho_f = 1000$ kg/m$^3$.

Following the derivation, the stress tensor z for the tissue is $$\tau = 2G\varepsilon + \lambda e I - pI$$

where $\varepsilon$ is the strain tensor, e is the volume dilation of the tissue, p is the local fluid pressure, $\lambda$ is a Lamé constant which characterizes the material along with the shear modulus G. Here, it is assumed that the tissue is a linear and isotropic elastic material. In terms of the displacement vector u, the strain tensor is written as $$\varepsilon = \frac{1}{2}(\nabla u + (\nabla u)^T)$$

and the volume dilation as $$e = \nabla \cdot u$$

Neglecting momentum and any external forces, the equation of motion is $$\nabla \cdot \tau = 0$$

Substituting the values of z, s and e gives $$G \nabla^2 u + (G+\lambda)\nabla(\nabla \cdot u) - \nabla p = 0$$

The elastic parameters (G,A) can be converted to the modulus of elasticity E and Poisson's ratio v:

$$G = \frac{E}{2(1+v)},$$

$$\lambda = \frac{Ev}{(1+v)(1-2v)},$$

leading to the elastic equation used by COMSOL:

$$\frac{E}{2(1+v)}\nabla^2 u + \frac{Ev}{2(1+v)(1-2v)}\nabla(\nabla \cdot u) = \nabla p$$

In the implementation of the elastic model in COMSOL, a two-dimensional simplification of the model is used, so the displacement has two components: u=(u, v). The "plane strain condition" assumes that strain exists in the x-y plane, while there is no displacement in the z-direction. This assumption is not appropriate for a fluid injection at a point, but it allows for simpler design and analysis. Once a sufficient model has been constructed in two dimensions, a three-dimensional model can be implemented using COMSOL's "Solid, Stress-Strain" application mode.

Values of E and v are taken from the elastic properties of soft tissue. A range of values is given for each parameter: 60 kPa<E<73 kPa and 0.3<v<0.5. For the disclosed models, values in the middle of the range E=65 kPa and v=0.4 are used.

In FIGS. 4A-4D, the continuum model is used to estimate the fluid movement and deformation in a 5 cm by 3 cm cross-section of tissue with a point source in the top center of this region. In order to simulate an infiltration, fluid is made to enter the tissue at a constant rate during times t=0 sec to t=10 sec. At t=10 sec the flow is stopped and the tissue begins to relax. Note that the model is two-dimensional, so flow rates are expressed in units of area per time rather than volume per time. No fluid is able to flow through the top and bottom boundaries which correspond to skin and bone, respectively. Fluid is able to move through the side boundaries to represent flow to the rest of the body. The bottom, left, and right boundaries are unable to move, while the top boundary, representing the skin, is able to swell outwards as the pressure increases.

Specific boundary and initial conditions must be expressed for both the fluid flow and elastic deformation equations. The boundary conditions for equations (3.3) and (3.4) are listed in Table 3.1.

TABLE 3.1

Continuum Model Boundary Conditions

| Boundary | Fluid Flow Condition | Elastic Deformation Condition |
|---|---|---|
| Left: | n · K∇p = $R_b$ ($P_b$ − P) | u = (0, 0) |
| Right: | n · K∇p = $R_b$ ($P_b$ − P) | u = (0, 0) |
| Top: | n · K∇p = 0 | u unspecified |
| Bottom: | n · K∇p = 0 | u = (0, 0) |

In Table 3.1, n is the unit vector pointing outward normal to the boundary, $R_b$ is the external conductance and $P_b$ is the external pressure. These conditions allow flow through the left and right boundaries state that flow is driven by the difference in the pressure in the tissue within the model region and the pressure outside of this region. Since the tissue outside of the region is large in comparison to the model domain, it is assumed that the exterior pressure stays at a constant value of $P_b = 0$ Pa. Higher values of $R_b$ correspond to easier flow out of the region, while lower values of $R_b$ result in lower flow. $R_b = 1$ m$^2$s/kg.

The condition u=(0, 0) states that the displacement along the boundary is 0, so the boundary's position is fixed. The condition where u is unspecified is called a free boundary condition. The initial conditions are set to $u_0 = (0, 0)$ and $p_0 = 0$.

Figure 4D:
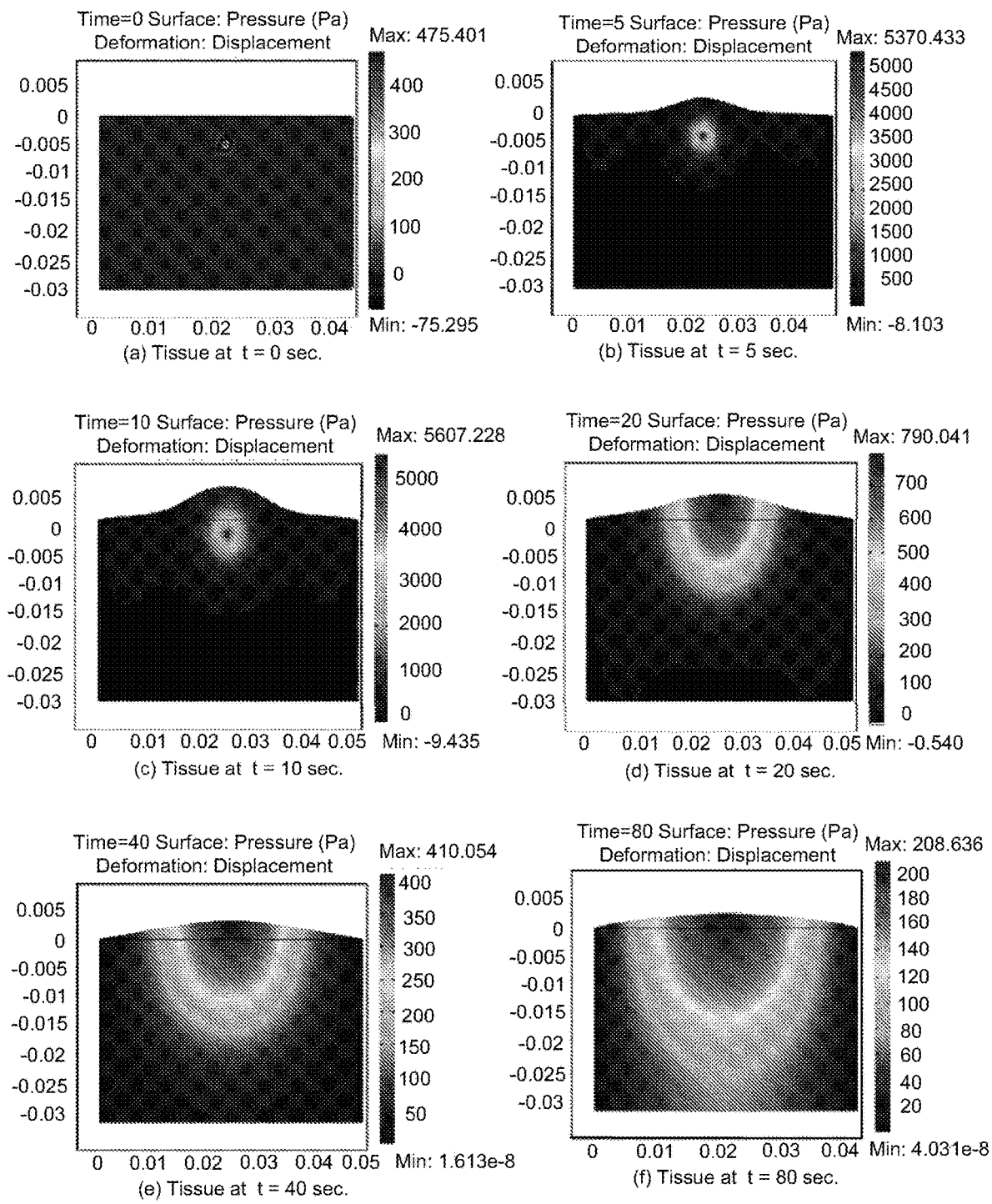
FIG. 4D illustrates a solution to the continuum model solution for pressure and displacement.

The model is defined in COMSOL using the parameters and boundary conditions described in the previous section. The model is solved numerically using an iterative method in which the pressure and displacement is calculated throughout the domain for many closely-spaced time steps. The solutions to the model at times t=0 sec, t=5 sec, t=10 sec, t=20 sec, t=40 sec, and t=80 sec are shown in FIG. 4D. The surface color corresponds to the pressure (red represents high pressure and blue represents low pressure) and the changing top boundary location corresponds to the deformation of the tissue. As expected, the pressure is highest near the injection site and decreases at a distance from the injection site. The solution in FIG. 4D also shows that as fluid is injected into the tissue the region swells up and then slowly returns to its original state after the infiltration is removed. This is shown in the displacement of the top boundary condition in the solution.

The continuum model solution provides spatial quantitative information concerning displacements, pressures and material movement within the porous ITS which may be compared with physical measurements both in the course of fine-tuning a compartment model as well as in direct use within an instrument system.

Figure 4E:
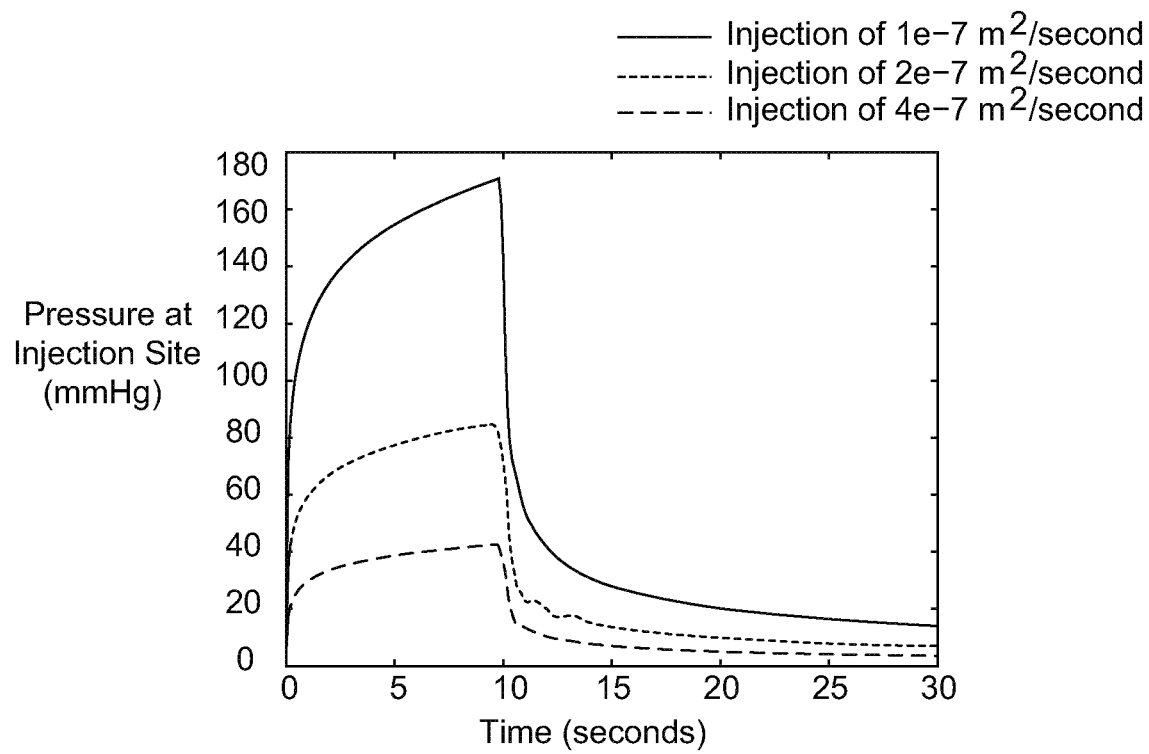
FIG. 4E illustrates predicted pressure at an infusion site region for three different injection rates.

Pressure at the injection site is plotted versus time in FIG. 4E for three different constant injection rates: $10^{-7}$, $2 \cdot 10^{-7}$, and $4 \cdot 10^{-7}$ m$^2$/s. The injection takes place between t=0 and t=10 sec. The plot shows that pressure increases monotonically during the infiltration (t=0 sec to t=10 sec) and then sharply declines after the infiltration is removed (t=10 sec).

Figure 4F:
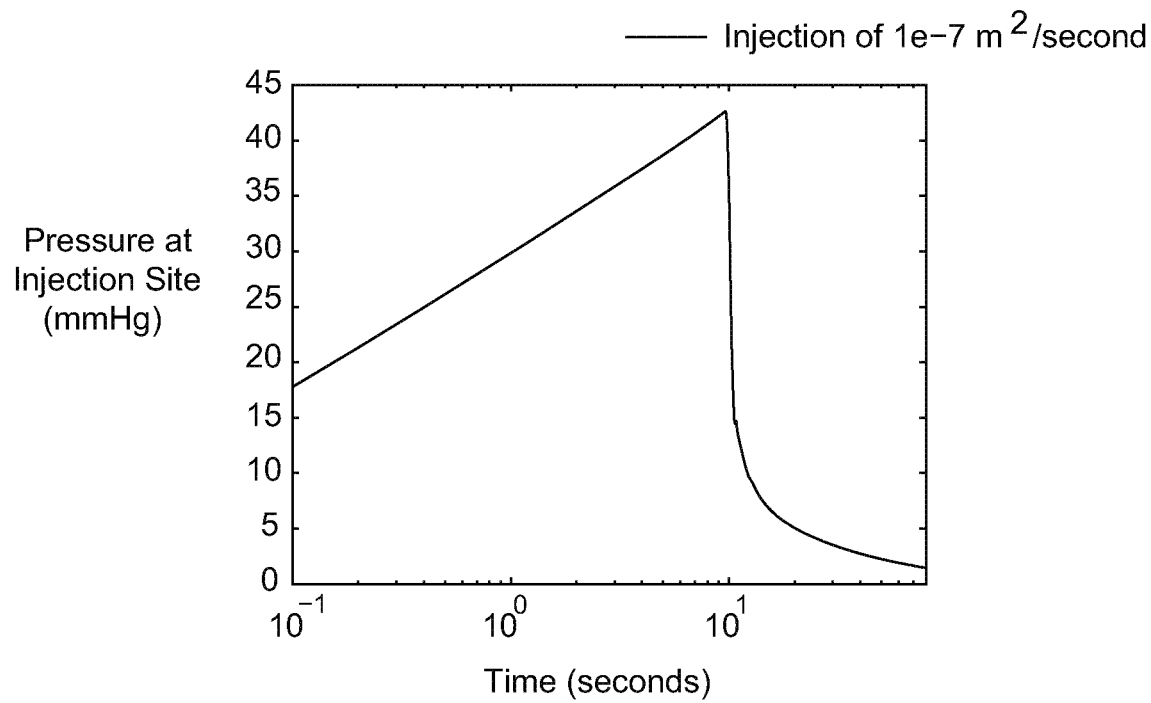
FIG. 4F illustrates predicted pressure at an infusion site region for a specified injection rate.
Figure 4G:
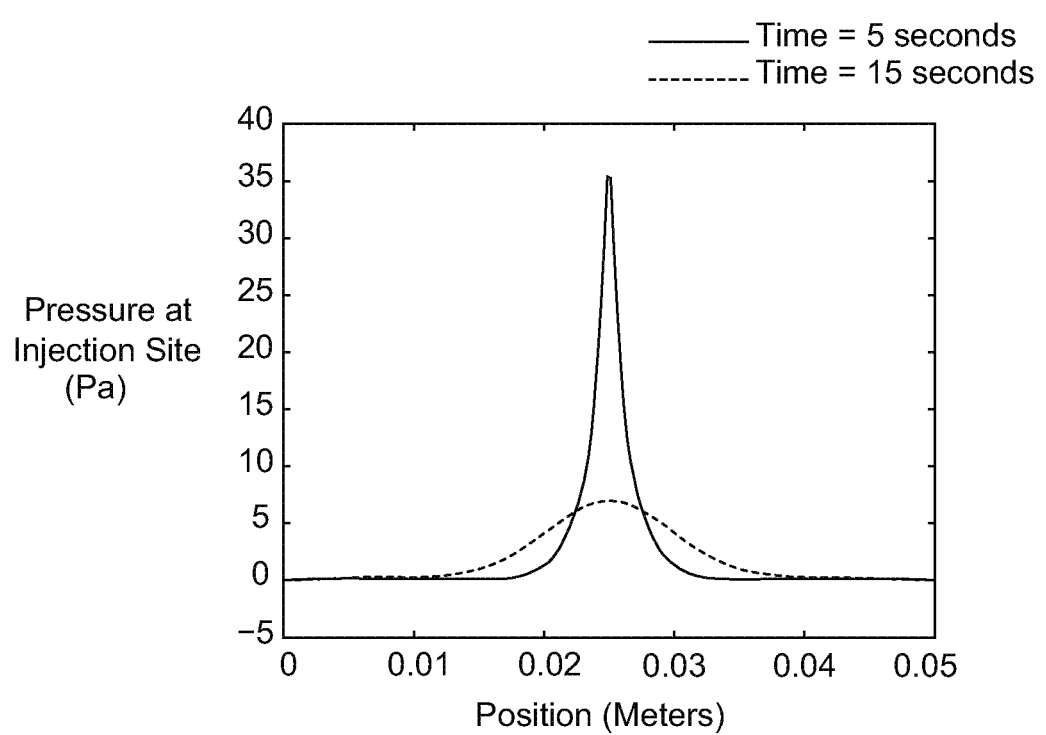
FIG. 4G illustrates pressure evaluated along a line passing through an infusion site region.

The pressure decreases until reaching the value of the external pressure in the rest of the body. Recall that this external pressure is specified in the side boundary conditions. Notice that the pressure does not increase linearly with time during the infiltration, but instead increases more slowly as time passes. This can be attributed to the tissue deformation. Because the volume of the tissue increases as more fluid is injected into the region, the same influx of fluid at later times does not increase the pressure as much as it did initially. FIG. 4F illustrates predicted pressure at the injection site for an injection rate of $10^{-7}$ m$^2$/s from t=0 to t=10 sec. Time is plotted on a logarithmic scale to show an approximately straight line for times earlier than t=10 sec. For an injection of a constant rate, the model predicts that the pressure at the injection site will grow according to a logarithmic function of time. FIG. 4F demonstrates that the pressure grows approximately according to a logarithmic function of time.

FIG. 4E illustrates pressure evaluated along a line passing through the injection site (x=0.025 meters). Plots are shown at t=5 (during infiltration) and at t=15 seconds (following infiltration) to demonstrate the stretching and relaxing of tissue. FIG. 4E demonstrates the spatial variance of pressure during and shortly following an infiltration. The pressure is evaluated along a line passing through the injection site (x=0.025 meters) for the constant injection rate $10^{-7}$ m$^2$/s. The two plots show pressure during infiltration at t=5 and shortly following infiltration at t=15 seconds. During infiltration, there is a sharp peak at the injection site, but following injection the peak quickly decreases as the fluid disperses throughout the region of tissue.

In addition to the two-dimensional fluid flow model presented in the previous two sections, a three-dimensional axisymmetric model can be used. The axisymmetric model uses the three-dimensional equations for poroelasticity in cylindrical polar coordinates (r, φ, z) but assumes that the variables do not vary with the angle φ. The model is then solved in the two-dimensional r-z plane and later mapped to three dimensions. The assumption of axial symmetry reduces the complexity of the model compared to a full three-dimensional model, reducing the difficulty and time of obtaining a solution.

Figure 4H:
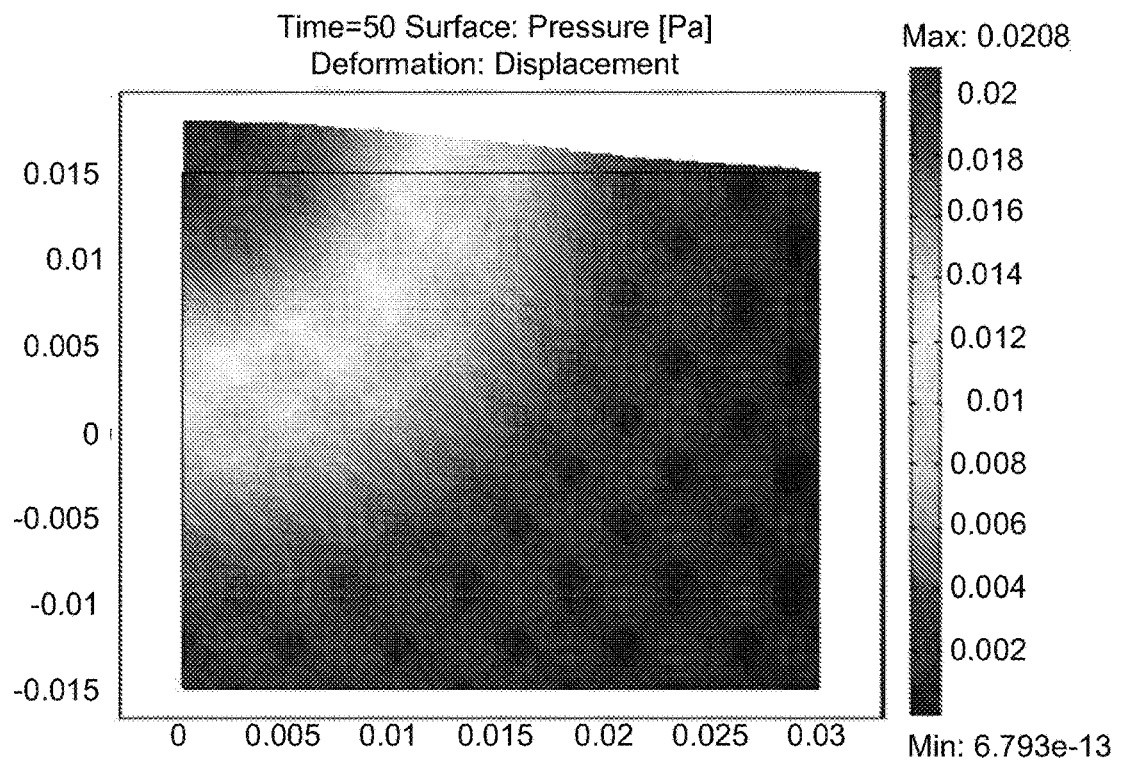
FIG. 4H illustrates an axisymmetric model in a two-dimensional plane.

FIG. 4H illustrates an axisymmetric model in the two-dimensional r-z plane. The solution is shown at t=50 seconds for an injection of fixed pressure 100 Pa from t=0 to t=10 seconds.

Figure 4I:
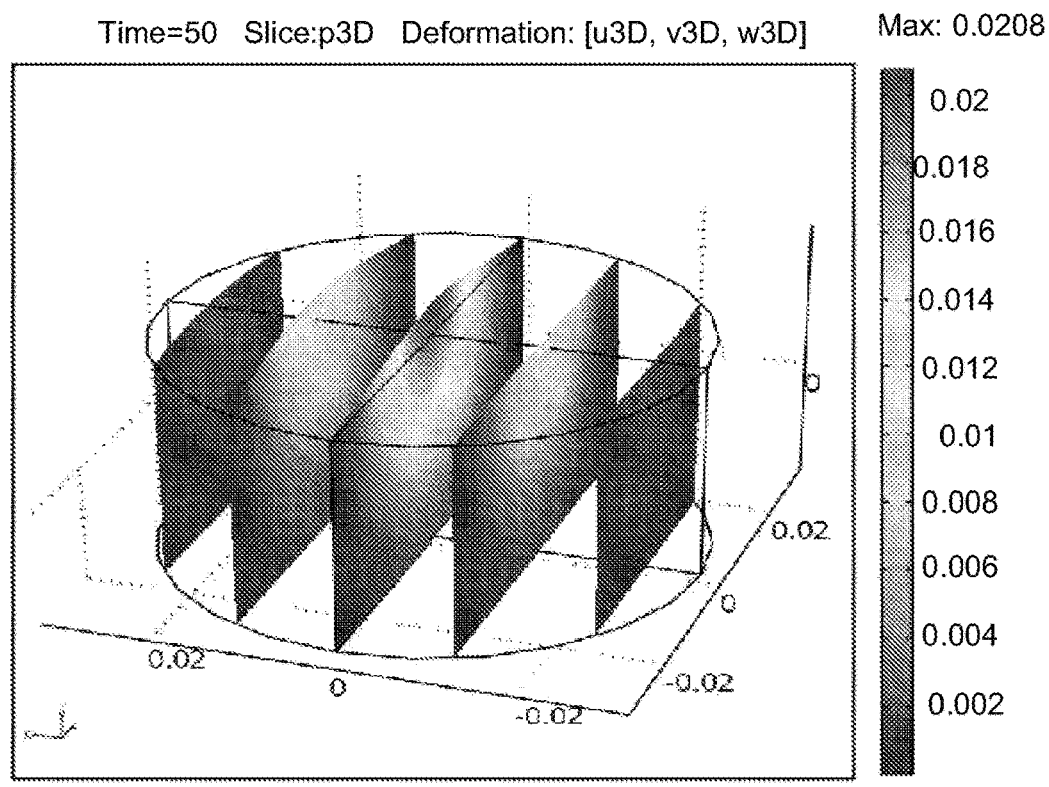
FIG. 4I illustrates an axisymmetric model mapped from the two-dimensional plane of FIG. 4H to a three dimensional place.

An example of a solution to the axisymmetric model is shown in FIG. 4I, which illustrates the axisymmetric model mapped from the two-dimensional r-z plane to three dimensions. The solution is shown at t=50 seconds for an injection of fixed pressure 100 Pa from t=0 to t=10 seconds. The axisymmetric model uses the same parameter values and boundary conditions as the two-dimensional models shown in earlier sections, with the exception that, instead of a flow source, a pressure source of 100 Pa is used at the center of the region.

Flow sources are not implemented at the symmetry axis r=0 because of the manner in which COMSOL treats flow sources in an axisymmetric domain.

In comparing the compartment model with the continuum model, the three compartment model tracks fluid volume and protein mass in three compartments: the vein (plasma), the interstitial tissue near the infiltration site, and the remainder of the body tissue. Fluid volumes in the tissue compartments are important because volume increases reflect deformation of the tissue and serve as a primary indicator of infiltration into the interstitial space. Protein mass influences the rate of change of volume between the three compartments, since different protein concentrations add to the osmotic gradient and drive fluid flow. In contrast, the continuum model provides the total deformation of each compartment and distribution of fluid throughout the body, but not the distribution of fluid or mass within each compartment.

In contrast, the continuum model shows distribution of fluid and pressure in a single compartment, but does not incorporate flow between compartments. No lymph or capillary activity is present in the presented form of the continuum model, though this may be accomplished by addition of an array of flow 'sinks' dispersed throughout a three dimensional model space. Here, flow due to pressure gradients or flux out of a compartment is seen.

The approaches complement each other since the compartment model simulates flow between distinct regions and the continuum model simulates flow within a region. The two models can be compared by using a compliance relationship to calculate pressure from volume in the compartment model. This gives continuous pressure output for both models that can be compared for identical inputs. Additionally, both models predict the expected increase in volume for a given fluid input. In this manner, they could both be used to predict the maximum flow rate above which infiltration will be harmful to a patient.

The three-compartment can be modified to reflect more realistic urination modeling, further sensitivity analysis, and parameter estimation for neonates and elderly patients. It can be further extended to a larger number of compartments if needed to provide higher resolution.

In certain embodiments, in the three-compartment model fluid loss from the body (urination and perspiration) and fluid input to the body (ingestion, infusion, and infiltration) is described in constant terms. Therefore, in order for the system to reach a steady state volume the fluid input is defined as equal to the fluid loss. This is realistic for describing the steady state volume, but might be unrealistic during infiltration events because the body adjusts urination to maintain equilibrium based on the venous plasma volume. When fluid is being infused directly into the tissue, less fluid enters the plasma and the venous plasma volume drops. Consequently, the urination rate should decrease as well. In certain embodiments, the urination rate could be modeled as a constant (a) plus a term proportional to the difference from normal plasma volume, i.e.

$$J_{ur} = \alpha + \beta(V_{PL} - V_{PL_0})$$

In certain embodiments, the disclosed model currently predicts the response to infiltrations of different flow rates and durations for adults. Parameters can be adjusted in order to predict the response of neonates and elderly patients to infiltrations. In certain embodiments, certain parameters may be varied if any differ most greatly between healthy adults, neonates, and elderly. This is particularly pertinent because most infiltrations occur in neonates and elderly patients.

In certain embodiments, the accuracy of the continuum model can adjusted. In certain embodiments, although the current model takes into account the increase in volume due to tissue deformation, the hydraulic conductivity is held constant. As tissue expands, the pores in the tissue become larger and allow easier flow, so in certain embodiments this behavior can be modeled by expressing the hydraulic conductivity as a function of tissue dilation where greater dilation leads to larger hydraulic conductivity values. In certain embodiments, hydraulic conductivity is expressed as K=H exp(Re) where K is the hydraulic conductivity, e is the tissue dilation, and H, and R are positive constants.

In certain embodiments, the continuum model does not directly account for lymph flow. Instead, the flow out of the tissue region is assumed to be a result of flow into the rest of the body. In certain embodiments, a flow rate out of the tissue representing the lymph flow is incorporated that could be based on the lymph flow relationship seen in the compartment model. In addition, for the side boundary conditions it is assumed that the pressure in the tissue outside of the region considered is held constant at p=0 Pa. In certain embodiments, this pressure increases as fluid flows out of the injection region into the rest of the body.

In certain embodiments, the continuum model could be expanded to describe a nonsymmetrical three-dimensional region of tissue. The current three-dimensional model describes a region of tissue with axial symmetry. In certain embodiments, flow is modeled in a full three-dimensional tissue model without a convergent solution. In certain embodiments, this model may involve systematically testing different solvers in COMSOL and varying the finite element mesh. Obtaining a solution in a basic cube or cylindrical geometry are focused on. In order to model an infiltration in the arm, the region 400 shown in FIG. 4A is considered. In certain embodiments, this kind of model is expanded to include different tissue types by varying parameter values in different regions.

Figure 5:
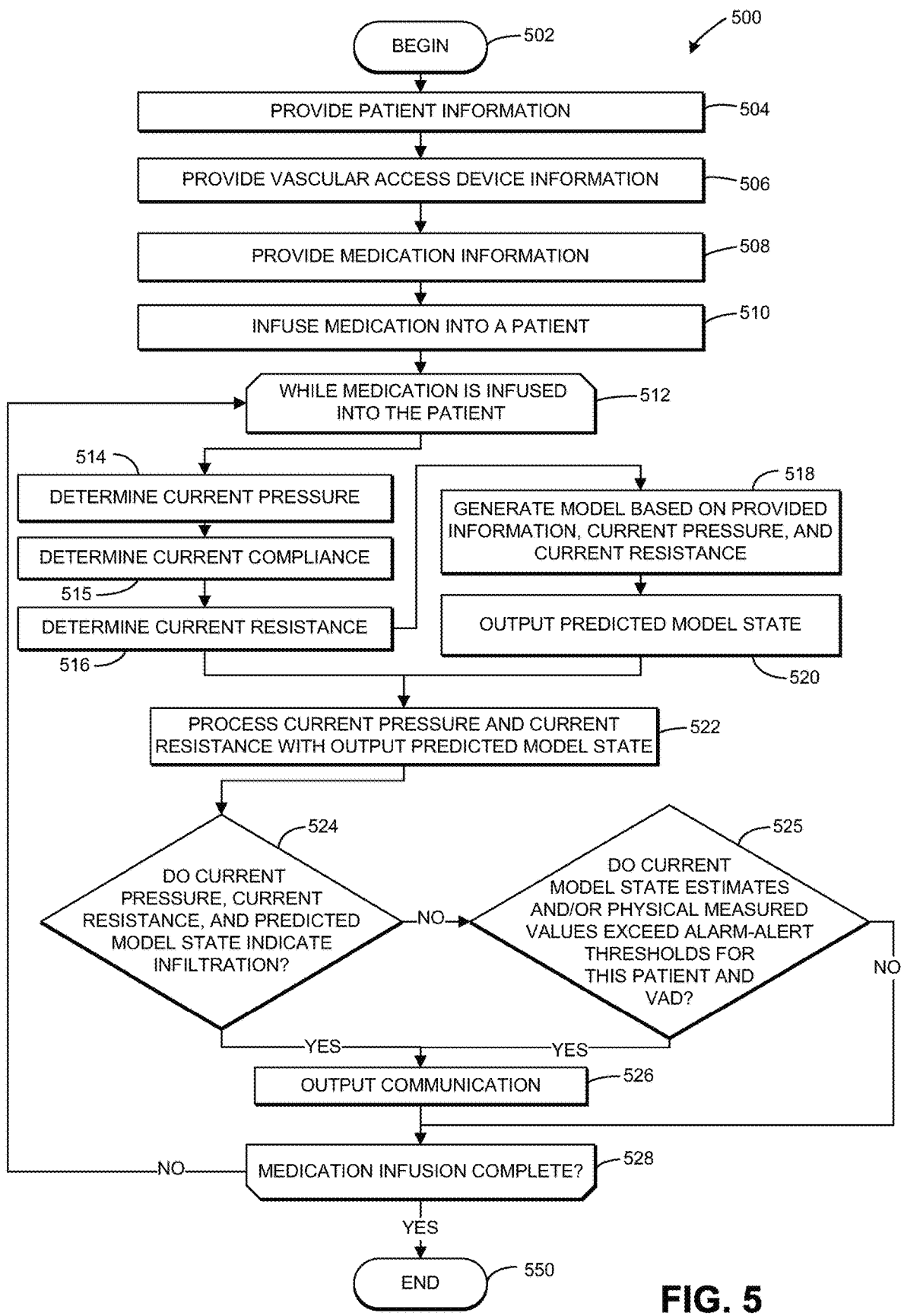
FIG. 5 is an exemplary process for monitoring the delivery of medication using the medication delivery monitoring system of FIG. 1.

FIG. 5 is an exemplary process 500 for monitoring the delivery of medication using the medication delivery monitoring system 100 of FIG. 1. In certain embodiments, the process 500 of FIG. 5 is embodied in processor 106 as computer-readable instructions configured to be stored in memory 120 (e.g., as software), which can then be loaded onto a system 100 or other machine as illustrated and described in FIG. 1.

The process 500 begins from step 502 and proceeds to steps 504, 506, and 508 in which patient information, VAD information, and medication information, respectively, are provided to the system 100. Next, in step 510, medication is infused into the patient 116. The process 500 proceeds to loop steps 512 to 528, which repeat as long as medication 118 is infused to the patient. In certain embodiments, the system 100 functions indifferently to the type of medication being infused, except for the potential to adjust response thresholds when certain highly vesicant medications, such as vincristine or adriamyacin, are being infused. In steps 514-516, the system 100 determines a current pressure, compliance, and resistance of the fluid delivery channel 110. In certain embodiments, other current values are determined. In step 518, a model is generated based on the provided information (e.g., the patient information, VAD information, and medication information), current pressure, and current resistance, and in step 520, a predicted model state of the infusion site region 114 is output. In certain embodiments, other information is output, such as an expected pressure and expected resistance of the infusion site region 114. In step 522, the current pressure and current resistance are processed with the predicted model state. If in decision step 524 the current pressure and current resistance, as compared to the predicted model state of the infusion site region 114, indicate an infiltration has occurred, then a communication is output in step 526. Otherwise, the process 500 proceeds to decision step 525, in which, if it is determined that the model state estimates and/or physical measured values exceed alarm-alert thresholds for the patient and VAD, then an appropriate communication is output in step 526. Otherwise, the process 500 proceeds to end loop step 528. If, in end loop step 528, the medication infusion is not complete, the process 500 returns to beginning loop step 512, otherwise the process 500 ends in step 530.

Having set forth in FIG. 5 a process 500 for monitoring the delivery of medication using the medication delivery monitoring system 100 of FIG. 1, an example will now be presented using the process 500 of FIG. 5 and an adult patient.

The process 500 begins from step 502 and proceeds to steps 504, 506, and 508 in which the adult patient information, VAD information, and medication information, respectively, are provided to the system 100. Next, in step 510, medication is infused into the patient 116. The process 500 proceeds to loop steps 512 to 528, which repeat as long as medication 118 is infused to the patient. As an example in steps 514-516, the system 100 measures a current pressure (which is equal to the flow times the resistance of the fluid delivery channel 110 plus any hydrostatic offset), a current resistance (which includes the sum of the VAD, connecting tubing and vessel resistance), and compliance of the delivery channel 110. In step 518 the compartment/and-or continuum models are employed to generate estimated states of the delivery system. In step 520 some or all of these values may be output for presentation via the user interface. In step 522, measured physical parameters including resistance, compliance and pressure integrated with output of the model for further decision logic operations in step 524. In certain embodiments, other current values are determined. In step 518, a model is generated based on the provided information (e.g., the patient information, VAD information, and medication information and the flow history), current pressure, and current resistance, and in step 520, a predicted model state of the infusion site region 114 is output, such as whether there is infused fluid in infusion site region, and possibly protein. In certain embodiments, other information is output, such as an expected pressure and expected resistance of the infusion site region 114. In decision step 524, the current pressure and current resistance are processed with the predicted model state. In step 526, a communication is output because a threshold of alarm for infiltration, as defined by a clinician as an estimated number of microliters per kilogram for an adult patient, is triggered. The medication infusion is indicated as complete in step 528, so the process 500 ends in step 530.

Another example will now be presented using the process 500 of FIG. 5 and a neonatal patient. The process 500 begins from step 502 and proceeds to steps 504, 506, and 508 in which the neonatal patient information, VAD information, and medication information, respectively, are provided to the system 100. Next, in step 510, medication is infused into the patient 116. The process 500 proceeds to loop steps 512 to 528, which repeat as long as medication 118 is infused to the patient. In steps 514-516, the system 100 determines a current pressure, a current resistance, of 2 mmHg/liter/h plus the catheter resistance, and compliance, a high compliance value of greater than 4 microliters/mmHg, of the fluid delivery channel 110. In certain embodiments, other current values are determined. In step 518, a model is generated based on the provided information (e.g., the patient information, VAD information, and medication information), current pressure, and current resistance, and in step 520, a predicted model state of the infusion site region 114 is output, such as whether there is infused fluid in infusion site region, and possibly protein. In certain embodiments, other information is output, such as an expected pressure and expected resistance of the infusion site region 114. In step 522, the current pressure and current resistance are processed with the predicted model state. In decision step 524 the current pressure and current resistance are processed with the predicted model state and do not indicate an infiltration, but in decision step 525 the current model state estimates and/or physical measured values exceed alarm-alert thresholds (as defined by a clinician as an estimated number of microliters per kilogram for a neonatal patient) for the patient and VAD, so a communication is output in step 526. The medication infusion is indicated as complete in step 528, so the process 500 ends in step 530.

Figure 6:
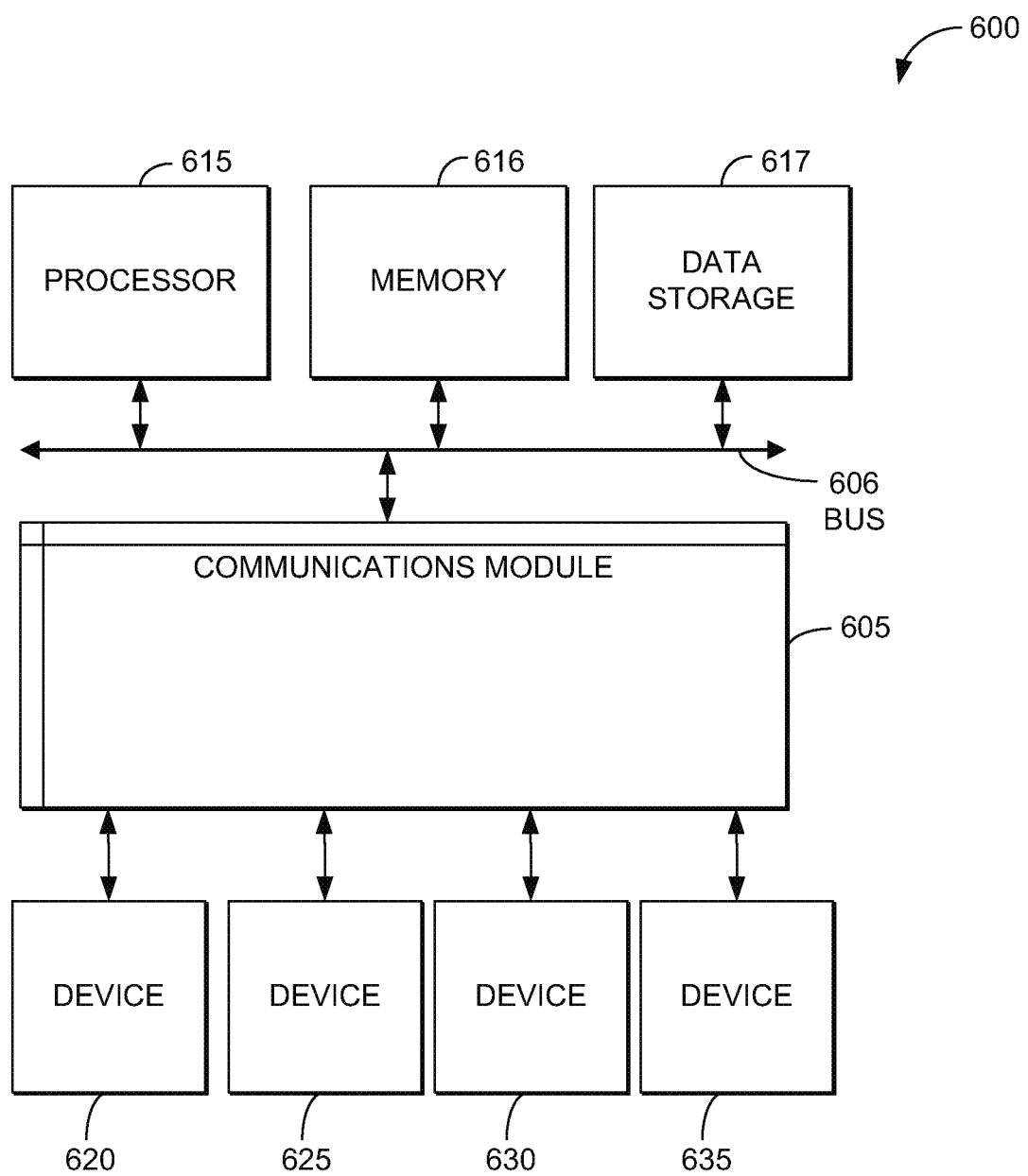
FIG. 6 is a block diagram that illustrates an exemplary computing system that can perform certain aspects of the present disclosure in accordance with one configuration of the present disclosure.

FIG. 6 is a block diagram that illustrates an exemplary computing system 600 that can perform certain aspects of the present disclosure in accordance with one configuration of the present disclosure. Computing system 600 may represent any one or more of system 100. The computing system 600 may include communications module 605 for communicating information, bus 606 for communicating information between different modules, and processor 615 coupled with the communications module 605 for processing information. Processor 615 may represent processor 106 of FIG. 1. The system 600 is configured to be coupled to a fluid pressure sensor device 630 of sufficient resolution, accuracy and bandwidth to measure fluid pressure in the fluid delivery channel 110 downstream (e.g., patient side) of the pump mechanism. The system 600 is also configured to couple to a fluid pumping mechanism device 635 and associated controlling electronic software and hardware to provide both continuous and modulated flow patterns supporting measurement of fluid flow resistance.

Computing system 600 may also be coupled to devices 620 and 625. One or more devices 620 may represent output device 108 of FIG. 1, and one or more devices 625 may represent user interface 102 of FIG. 1. Computing system may 600 further include memory 616, such as a RAM, a ROM or other memory device, coupled to bus 606, for storing information and instructions to be executed by processor 615. Memory 616 may also be used for storing temporary variable or other intermediate information during execution of instructions to be executed by processor 615. Computing system 600 may further include data storage device 617, such as a magnetic disk or optical disk, coupled to bus 606 for storing information and instructions. Memory 616, data storage 617, or both may represent memory 120 of FIG. 1.

The embodiments of the present disclosure provide a system for monitoring an infusion site region of a patient and for determining state estimates and measurements associated with the risk that the infusion site has become infiltrated by the improper positioning of the VAD and/or the erosion of the vessel puncture site. The system may further provide alarms and alerts based on the severity of the risk measured. The determinations are made based at least in part on the comparison of one or more model estimates of states of fluids and/or protein content in the within the body with an expected value of these states determined at least in part from information concerning the patient such as weight, age, IV site location and catheter. The determination additionally may be based on the measurement of current values and rates of change of pressure and resistance to flow of the infusion site combined such as by Boolean logic with the previously mentioned model estimates. The plurality of expected fluid delivery state estimates are determined using a model of the infusion site region, such as a compartment or continuum model implemented through a finite element computation method. If the system determines the that risk that an infiltration has occurred exceeds either an alert or an alarm threshold determined at least in part through compu-tations based on patient information including but not limited to age and/or weight and/or VAD position and/or medication, then the system outputs an alert or alarm such as an visible or audible alarm, so that an operator can take appropriate action in response to the infiltration. The system is also able to present the current state(s) and measures of the IV delivery system in graphical or numerical form, such as, for example, the current estimate of the IV fluid disposed outside the vein as computed by the model may be presented to the clinician for their own judgment as to risk to the patient.

Although the term "processor" is used in various places in the description of preferred embodiments, such term is meant to apply to one or more devices that perform processing and is not necessarily limited to a single device located at one location. The term "processor" may include multiple processing devices located at locations separate from each other. A processor may be a general-purpose microprocessor, a microcontroller, a digital signal processor ("DSP"), an application specific integrated circuit ("ASIC"), a field programmable gate array ("FPGA"), a programmable logic device ("PLD"), a controller, a state machine, gated logic, discrete hardware components, or any other suitable device that can perform calculations or other manipulations of information. A processor may also include one or more machine-readable media for storing software. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media may include storage integrated into a processor, such as might be the case with an ASIC. Machine-readable media may also include storage external to a processor, such as a random access memory ("RAM"), a flash memory, a read-only memory ("ROM"), a programmable read-only memory ("PROM"), an erasable PROM ("EPROM"), registers, a hard disk, a removable disk, a CD-ROM, a DVD, or any other suitable storage device. In addition, machine-readable media may include a transmission line or a carrier wave that encodes a data signal. Those skilled in the art will recognize how best to implement the described functionality for a processor. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. Instructions can be, for example, a computer program including code. A machine-readable medium may comprise one or more media. Furthermore, "medication" is not meant to be restrictive but is meant to include any fluids administered to a patient.

Computer program code for carrying out operations as discussed above can be written in an object oriented programming language such as, for example, JAVA™, Smalltalk, or C++. However, the computer program code for carrying out operations may also be written in conventional procedural programming languages, such as the "C" programming language, in an interpreted scripting language, such as Perl, or in a functional (or fourth generation) programming language such as Lisp, SML, Forth, or the like. The software may also be written to be compatible with HLA-7 requirements.

It is understood that although the present disclosure has been described in embodiments, various modifications of the illustrative embodiments, as well as additional embodiments of the disclosure, will be apparent to persons skilled in the art upon reference to this description without departing from the scope of the disclosure, as recited in the claims appended hereto. It is contemplated that the appended claims will cover any such modifications or embodiments as fall within the scope of the disclosure.

The invention claimed is:

1. A medication delivery monitoring device comprising:
a sensor that measures a plurality of fluid state parameters of a fluid delivery channel through which a medication is delivered to an infusion site region of a patient; and
a processor that (i) creates a model of a state of the infusion site region, comprising fluid state parameters of interstitial tissue at the infusion site region, based on the measured fluid state parameters and received input information, wherein the model comprises a determination of an osmotic gradient component indicative of a difference in a protein concentration across a membrane of the fluid delivery channel, and (ii) provides a communication to an output device if the measured fluid state parameters at the infusion site region are not within expected infusion site region parameters.

2. The medication delivery monitoring device of claim 1, wherein the model of a state of the infusion site region comprises an uninfiltrated and infiltrated states.

3. The medication delivery monitoring device of claim 1, wherein the input information comprises any of patient information, medication delivery device information, and medication information.

4. The medication delivery monitoring device of claim 3, wherein the medication information comprises at least one of a chemical nature of the medication, a concentration of the medication, a rate of infusion of the medication, and a nature of at least one diluent or additive associated with the medication.

5. The medication delivery monitoring device of claim 3, wherein the medication delivery device information comprises at least one of a type of the medication delivery monitoring device, a dimension of the medication delivery monitoring device, and a location of the medication delivery monitoring device.

6. The medication delivery monitoring device of claim 1, wherein the fluid state parameters comprises any of pressure, resistance, capacitance, and impedance of the fluid delivery channel.

7. The medication delivery monitoring device of claim 6, wherein the resistance is measured based on small scale modulations, introduced by the processor, in an average infusion rate of the medication.

8. The medication delivery monitoring device of claim 7, wherein the small scale modulations are associated with resulting pressure variations in the fluid delivery channel to further measure capacitance and impedance at an input to the fluid delivery channel.

9. The medication delivery monitoring device of claim 1, wherein the sensor is an outlet pressure sensor.

10. The medication delivery monitoring device of claim 1, wherein the processor records any of instantaneous liquid state parameters, filtered fluid state parameters, and long term trends of fluid state parameters.

11. The medication delivery monitoring device of claim 1, wherein the model is any of a discrete compartment model and a continuum model.

12. The medication delivery monitoring device of claim 1, wherein the state of the infusion site region comprises any of an amount of fluid added to an interstitial space, an amount of protein transported, and expected pressure values.

13. The medication delivery monitoring device of claim 1, wherein the state of the infusion site region comprises protein mass in the interstitial tissue at the infusion site region.

14. The medication delivery monitoring device of claim 1, wherein the output device is a display configured to illustrate any of a measured and an expected fluid state parameters throughout a time the medication is infused into the patient.

15. The medication delivery monitoring device of claim 1, comprising a memory configured to store a history of the measured fluid state parameters, wherein the model is further based on the history of the measured fluid state parameters.

16. A medication delivery monitoring device comprising:
a sensor that measures a plurality of fluid state parameters of a fluid delivery channel through which a medication is delivered to an infusion site region of a patient, wherein the fluid state parameters comprise pressure and resistance;
an output device; and
a processor that (i) creates a model of a state of the infusion site region, comprising fluid state parameters of interstitial tissue at the infusion site region, based on the measured fluid state parameters and received input information that includes patient information, wherein the model comprises a determination of an osmotic gradient component of fluid flow, the osmotic gradient component indicative of a difference in a solute concentration across a membrane of the fluid delivery channel, and (ii) provides a communication to the output device if the measured fluid state parameters at the infusion site region are not within the model of a state of the infusion site region.

17. The medication delivery monitoring device of claim 16, wherein the input information further comprises any of medication delivery device information and medication information.

18. The medication delivery monitoring device of claim 16, wherein the fluid state parameters further comprise any of capacitance and impedance of the fluid delivery channel.

19. The medication delivery monitoring device of claim 16, wherein the sensor is a pressure sensor at an outlet of the fluid delivery channel.

20. The medication delivery monitoring device of claim 16, wherein the state of the infusion site region comprises protein mass in the interstitial tissue at the infusion site region.

21. The medication delivery monitoring device of claim 16, comprising a memory configured to store a history of the measured fluid state parameters, wherein the model is further based on the history of the measured fluid state parameters.

* * * * *